United States Patent
Thompson et al.

(12) 
(10) Patent No.: US 12,102,358 B2
(45) Date of Patent: Oct. 1, 2024

(54) LATERAL VERTEBRAL LUMBAR PLATE SYSTEM WITH INTEGRATED ROTATIONAL CONTROL MECHANISM FOR SCREW RETENTION

(71) Applicant: Kyocera Medical Technologies, Inc., Redlands, CA (US)

(72) Inventors: Joseph Thompson, Round Rock, TX (US); Gary W. Klepač, Bertram, TX (US)

(73) Assignee: Kyocera Medical Technologies, Inc., Redlands, CA (US)

( * ) Notice: Subject to any disclaimer, the term of this patent is extended or adjusted under 35 U.S.C. 154(b) by 0 days.

(21) Appl. No.: 18/207,202

(22) Filed: Jun. 8, 2023

(65) Prior Publication Data

US 2023/0310041 A1    Oct. 5, 2023

Related U.S. Application Data

(63) Continuation of application No. 17/173,592, filed on Feb. 11, 2021, now Pat. No. 11,701,149.

(60) Provisional application No. 62/976,448, filed on Feb. 14, 2020.

(51) Int. Cl.
*A61B 17/80* (2006.01)
*A61B 17/70* (2006.01)

(52) U.S. Cl.
CPC ...... *A61B 17/7059* (2013.01); *A61B 17/8042* (2013.01); *A61B 17/8052* (2013.01)

(58) Field of Classification Search
CPC ............ A61B 17/8033; A61B 17/8042; A61B 17/8052; A61B 17/8057; A61B 17/7059
See application file for complete search history.

(56) References Cited

U.S. PATENT DOCUMENTS

| 2010/0145459 A1 | 6/2010 | McDonough et al. |
| 2012/0158058 A1 | 6/2012 | Michelson |

(Continued)

FOREIGN PATENT DOCUMENTS

| KR | 20190125844 A | 11/2019 |

OTHER PUBLICATIONS

Jun. 3, 2021 International Search Report issued in International application No. PCT/US2021/017570.

*Primary Examiner* — Si Ming Ku
(74) *Attorney, Agent, or Firm* — Clements Bernard Walker; Christopher L. Bernard; Devin Cummins

(57) ABSTRACT

A plate system includes a retention cap and a plate. The retention cap includes a head with tangs and a shank. The shank includes protrusions at an end of the shank and relief cut-outs clocked relative to the protrusions. The plate includes screw holes and a locking feature. The locking feature includes an assembly guide adapted to guide the shank and features thereof into the locking feature, locking detents distal to the top surface of the plate and adapted to receive the protrusions and interfere with rotational movement of the retention cap, and a retainer positioned axially between the assembly guide and the locking detents. The retainer is adapted to prevent axial movement of the retention cap. The locking feature is adapted to hold the retention cap with the tangs overlapping the screw holes and with the tangs not overlapping the screw holes.

15 Claims, 20 Drawing Sheets

(56) References Cited

U.S. PATENT DOCUMENTS

| | | | |
|---|---|---|---|
| 2015/0025635 A1* | 1/2015 | Laubert | A61F 2/447 29/428 |
| 2018/0310966 A1* | 11/2018 | Altarac | A61B 17/80 |
| 2020/0038068 A1 | 2/2020 | Altarac et al. | |

* cited by examiner

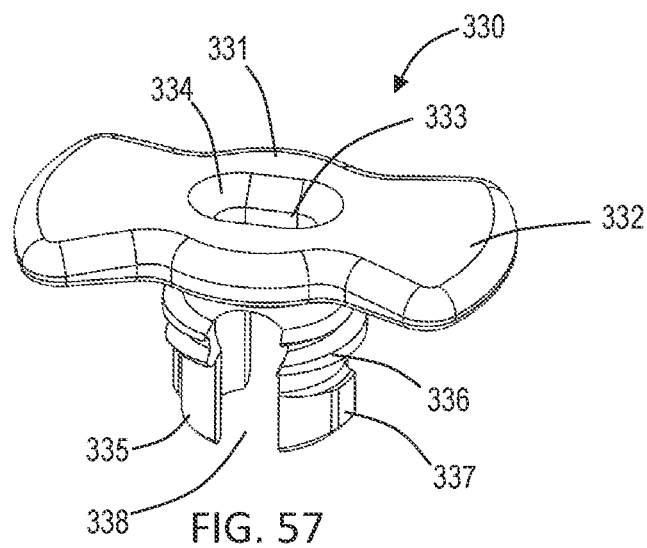
FIG. 57
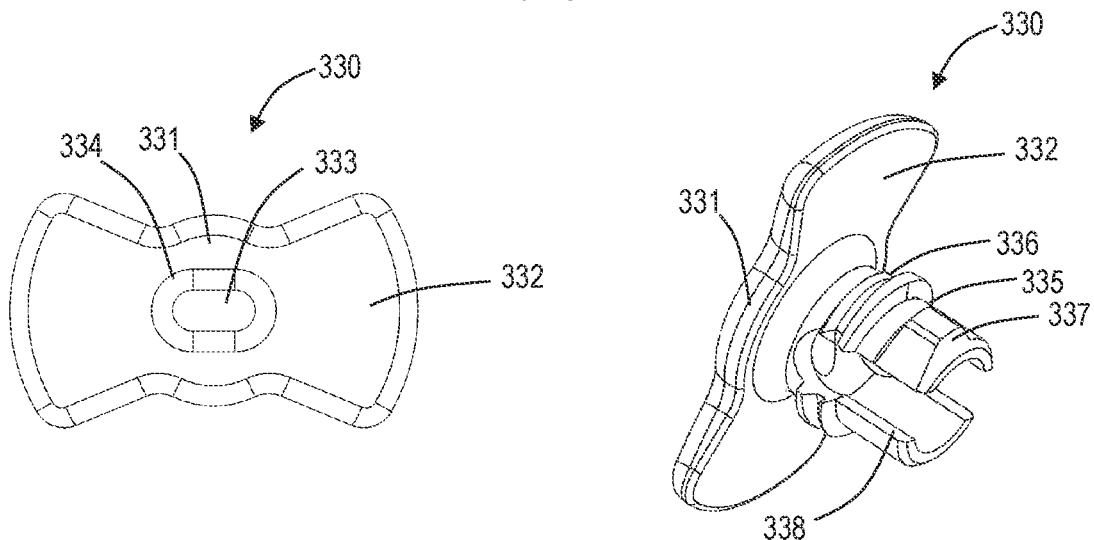
FIG. 58
FIG. 59
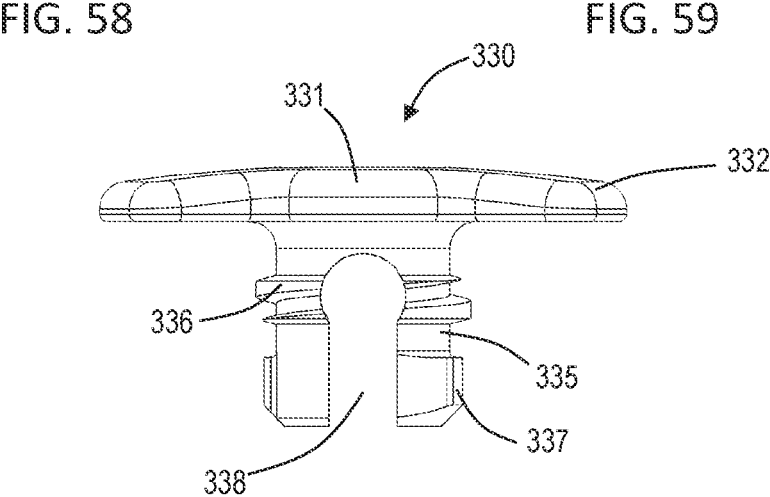
FIG. 60

LATERAL VERTEBRAL LUMBAR PLATE SYSTEM WITH INTEGRATED ROTATIONAL CONTROL MECHANISM FOR SCREW RETENTION

CROSS-REFERENCE TO RELATED APPLICATION

This application is a continuation of co-pending U.S. patent application Ser. No. 17/173,592, filed Feb. 11, 2021, and entitled "LATERAL VERTEBRAL LUMBAR PLATE SYSTEM WITH INTEGRATED ROTATIONAL CONTROL MECHANISM FOR SCREW RETENTION," which claims the benefit of priority of U.S. provisional patent application Ser. No. 62/976,448, filed on Feb. 14, 2020, and entitled "LATERAL VERTEBRAL LUMBAR PLATE SYSTEM WITH INTEGRATED ROTATIONAL CONTROL MECHANISM FOR SCREW RETENTION." The contents of each of U.S. patent application Ser. No. 17/173,592 and U.S. provisional patent application Ser. No. 62/976,448 are incorporated in full by reference herein.

TECHNICAL FIELD

The present disclosure generally relates to a lateral vertebral lumbar plate system. More particularly, the present disclosure relates to a lateral vertebral lumbar plate system with an integrated rotational control mechanism for screw retention.

BACKGROUND

During lumbar surgery, a plate is secured in a lateral position relative to the vertebrae using bone screws. If the bone screws do not stay in position and back out to any degree, the plate can move, which can negatively affect the healing process. Further, if retention caps do not remain securely over the heads of the bone screws, the bone screws can partially back out.

The above-described background relating to lumbar surgery is merely intended to provide a contextual overview of some current issues and is not intended to be exhaustive. Other contextual information may become apparent to those of ordinary skill in the art upon review of the following description of exemplary embodiments.

SUMMARY

The present disclosure generally provides a spinal thoracolumbar interbody lateral fixation system for securing to the vertebrae or other osseous material. The system is an assembly of multiple components: a thin metal plate, one or more retention caps, and multiple screws. The system is used in a direct lateral lumbar surgical approach. The system exhibits a novel rotational control mechanism that enables ease-of-manufacturing, disassembly prevention, and ease-of-usage for the surgeon end-user.

The one or more retention caps prevent screw-backout when engaged in the locked position, while allowing screws to be inserted/removed while in an unlocked position. During engagement, the retention cap locking mechanism provides disassembly resistance and also provides tactile feedback while rotating each of the one or more retention caps from the engaged position using a mating driver instrument.

A removable, thread-captured bolt connects the plate with a mating intervertebral body fusion device (IBFD). Two protrusions on the plate's medial underside allow for rotational alignment with the IBFD.

In one exemplary embodiment, the present disclosure provides a lateral lumbar plate system for securing to a vertebrae or other osseous material. The lateral vertebral lumbar plate system includes a retention cap and a lumbar plate. The retention cap includes a head and a shank. The head includes tangs. The shank extends from the head and includes protrusions distal to the head and relief cut-outs extending towards the head from an end of the shank distal to the head. The relief cut-outs are clocked relative to the protrusions. The lumbar plate includes screw holes and a locking feature. The screw holes are adapted to receive bone screws. The locking feature includes an assembly guide, locking detents, and a retainer. The assembly guide is proximal to a top surface of the lumbar plate and is adapted to guide the shank and features thereof into the locking feature. The locking detents distal to the top surface of the lumbar plate and adapted to receive the protrusions and interfere with rotational movement of the retention cap. The retainer is positioned axially between the assembly guide and the locking detents. The retainer is adapted to prevent axial movement of the retention cap. In a first rotational alignment of the retention cap relative to the lumbar plate, the tangs are positioned between screw holes so as to not axially overlap with the screw holes, and in a second rotational alignment of the retention cap relative to the lumbar plate, the tangs are positioned at least partially over the screw holes.

In embodiments, the assembly guide comprises axially extending insertion-assembly slots circumferentially aligned with a set of female detents and adapted to guide the protrusions through the locking feature to the set of locking detents. Optionally, the locking detents include a second set of female detents clocked from the first set of female detents and the insertion-assembly slots, the second set of female detents adapted to receive the protrusions while the retention cap is in the first rotational alignment and the second rotational alignment.

In embodiments, the retainer includes an annular extending rib adapted to axially interfere with the protrusions to prevent axial movement of the retention cap.

In embodiments, the assembly guide comprises an internal thread adapted to guide the shank into the locking feature via an external thread on the shank, and wherein the retainer comprises a blind recess bore adapted to receive the external thread therein to prevent backout of the retention cap. Optionally, the locking detents comprise a clocking star-pattern adapted to limit rotation of the retention cap to one direction, the one direction matching a threading direction for threading the shank into the locking feature.

In embodiments, the locking feature is centrally located in the lumbar plate between the screw holes. And in embodiments, the lateral vertebral lumbar plate system further includes a second retention cap, the lumbar plate includes a second locking feature and, the locking feature and the second locking feature are symmetric about a transverse plane of the lumbar plate In another exemplary embodiment, the present disclosure provides a method for lateral surgery. The method includes providing a lateral vertebral lumbar plate system. The method also includes sliding the lumbar plate system down one of a central shaft instrument and K-wire that is inserted into an intervertebral space. The method also includes driving bone screws through the screw holes until the bone screws are seated within the screw holes. The method further includes rotating the retention cap from a first rotational alignment relative to the lumbar plate where the tangs are positioned between the screw holes so as to not axially overlap with the screw holes to a second rotational alignment relative to the lumbar plate where the tangs are positioned at least partially over the screw holes and over heads of the bone screws.

In a further exemplary embodiment, the present disclosure provides a lateral vertebral lumbar plate system for securing to a vertebrae or other osseous material. The lateral vertebral lumbar plate system includes a retention cap and a lumbar plate. The retention cap includes a head and a shank. The head includes tangs. The shank extends from the head. The shank includes protrusions distal to the head and relief cut-outs extending towards the head from an end of the shank distal to the head. The relief cut-outs are clocked relative to the protrusions. The lumbar plate includes screw holes and a locking feature. The screw holes are adapted to receive bone screws. The locking feature includes axially extending insertion-assembly slots, locking detents, and an annular extending rib. The axially extending insertion-assembly slots are proximal a top surface of the lumbar plate and are adapted to guide the protrusions into the locking feature. The locking detents are distal to the top surface of the lumbar plate and are adapted to receive the protrusions and interfere with rotational movement of the retention cap. The angular extending rib is positioned adjacent to the locking detents closer to the top surface of the lumbar plate than the locking detents. The angular extending rib is adapted to prevent axial movement of the retention cap. In a first rotational alignment of the retention cap relative to the lumbar plate, the tangs are positioned between screw holes so as to not axially overlap with the screw holes, and in a second rotational alignment of the retention cap relative to the lumbar plate, the tangs are positioned at least partially over the screw holes.

In embodiments, the axially extending insertion-assembly slots circumferentially align with a set of female detents, the axially extending insertion-assembly slots being adapted to guide the protrusions through the locking feature to the set of locking detents. Optionally, the locking detents include a second set of female detents clocked from the first set of female detents and the insertion-assembly slots, the second set of female detents being positioned under the annular extending rib and adapted to receive the protrusions while the retention cap is in the first rotational alignment and the second rotational alignment.

In embodiments, the axially extending insertion-assembly slots extend axially through the annular extending rib.

BRIEF DESCRIPTION OF THE DRAWINGS

The present disclosure is illustrated and described herein with reference to the various drawings, in which like reference numbers are used to denote like system components/ method steps, as appropriate, and in which:

FIG. 57 is a perspective view of the retention cap of the lumbar plate system of FIGS. 48 and 49;

FIG. 58 is a top view of the retention cap of FIG. 57;

FIG. 59 is a bottom perspective view of the retention cap of FIGS. 57-58;

FIG. 60 is a side view of the retention cap of FIGS. 57-59;

DESCRIPTION OF EXEMPLARY EMBODIMENTS

In various embodiments, the present disclosure relates a spinal thoracolumbar interbody lateral fixation system for securing to the vertebrae or other osseous material during lateral surgery. The lumbar plate system is an assembly of a lumbar plate, one or more retention caps, and multiple bone screws. The lumbar plate system is used in a direct lateral lumbar surgical approach. The lumbar plate system exhibits a novel rotational control mechanism that enables ease-of-manufacturing, disassembly prevention, and ease-of-usage for the surgeon end-user. In particular, the lumbar plate system includes a locking feature that includes an assembly guide proximal a top surface of the lumbar plate that is adapted to guide the retention cap into the locking feature, locking detents distal to the top surface of the lumbar plate that are adapted to receive protrusions of the retention cap and interfere with rotational movement of the retention cap, and a retainer positioned axially between the assembly guide and the locking detents that is adapted to prevent axial movement of the retention cap. Due to the combination of features, the lumbar plate system is easily assembled and easily actuated from an unlocked to a locked state for securing the bone screws in their seated positions while the retention cap is retained axially to prevent back-out of the retention cap and the bone screws.

Figure 1:
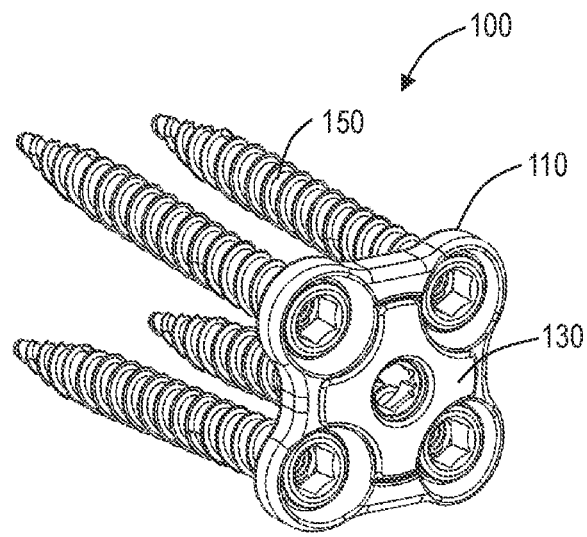
FIG. 1 is a perspective view of one exemplary embodiment of the lumbar plate system of the present disclosure in an unlocked state.
Figure 2:
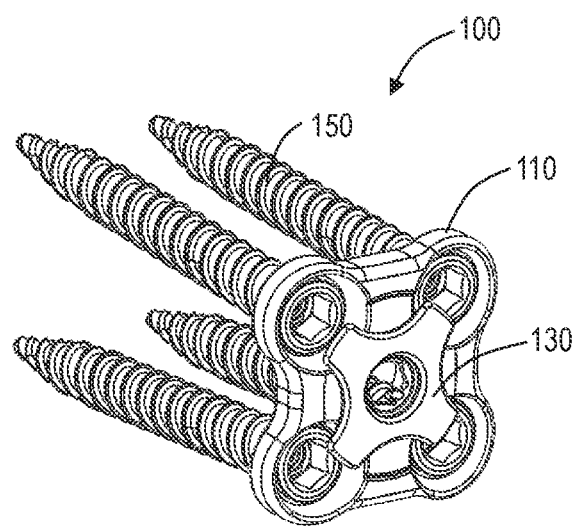
FIG. 2 is a perspective view of the lumbar plate system of FIG. 1 in a locked state.
Figure 3:
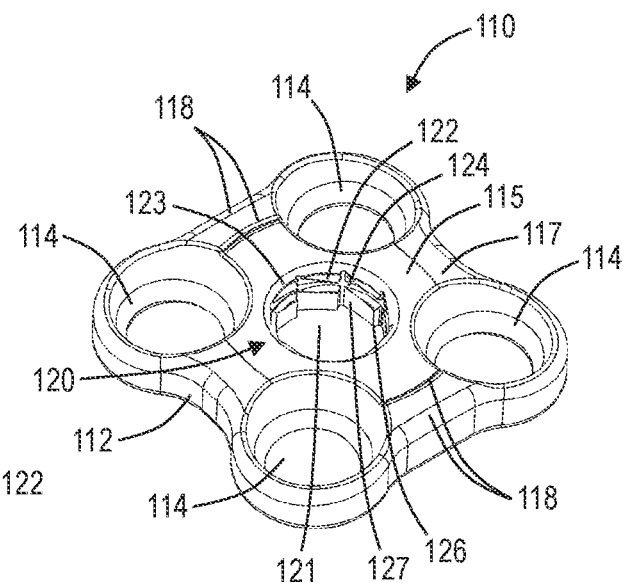
FIG. 3 is a perspective view of the lumbar plate of the lumbar plate system of FIGS. 1 and 2.
Figure 4:
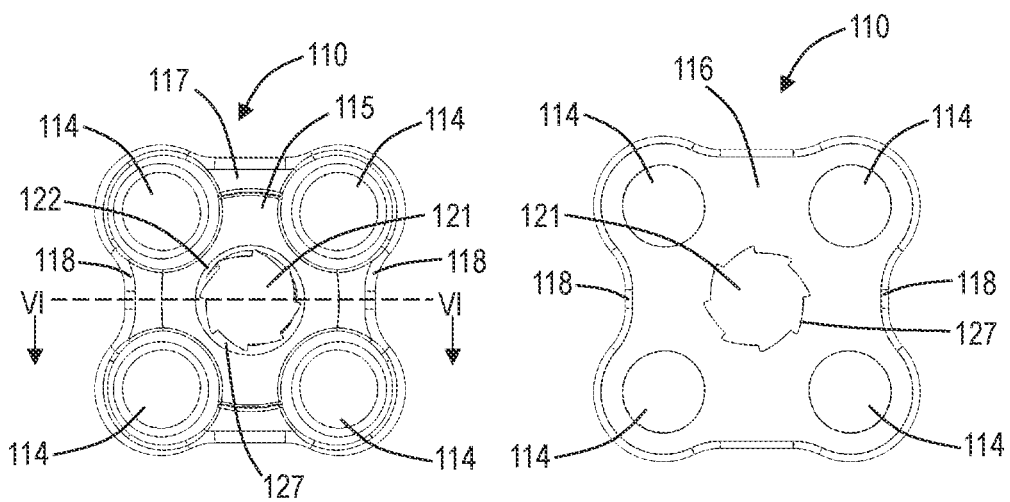
FIG. 4 is a top view of the lumbar plate of FIG. 3.
Figure 5:
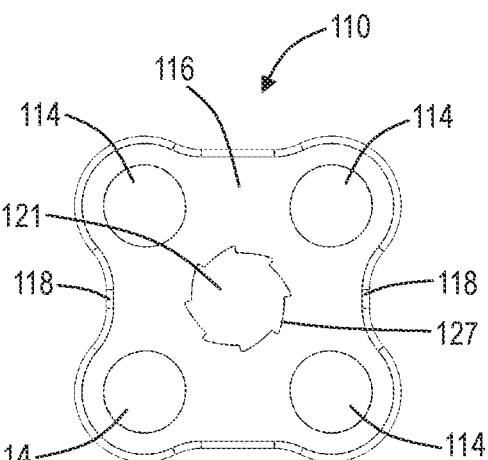
FIG. 5 is a bottom view of the lumbar plate of FIGS. 3-4.
Figure 6:
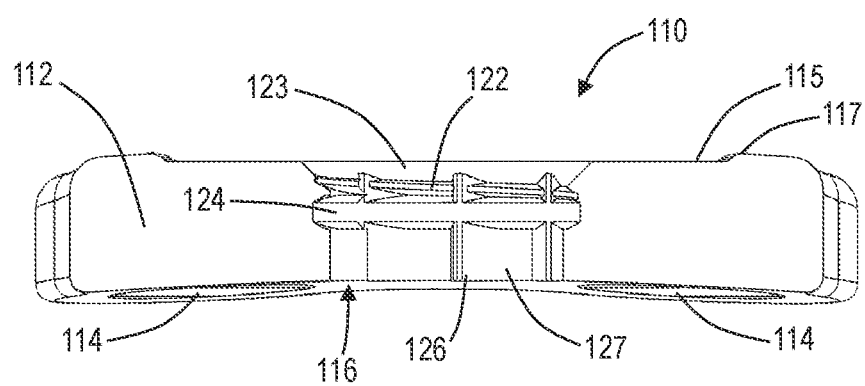
FIG. 6 is a cross-sectional view of the lumbar plate of FIGS. 3-5 taken along the line VI-VI in FIG. 4.
Figure 7:
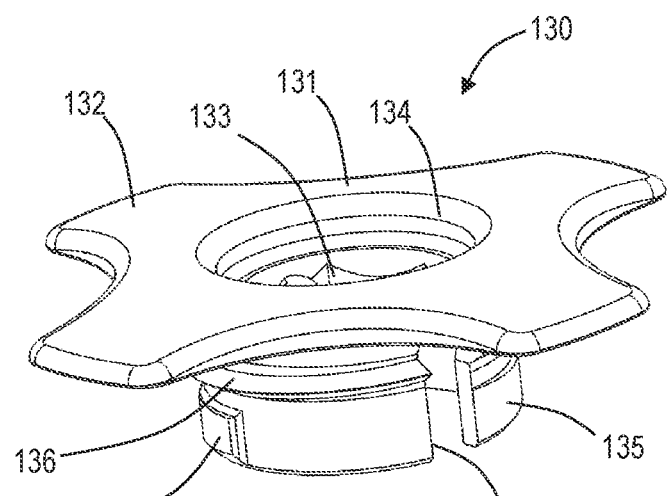
FIG. 7 is a perspective view of the retention cap of the lumbar plate system of FIGS. 1 and 2.
Figures 8, 9:
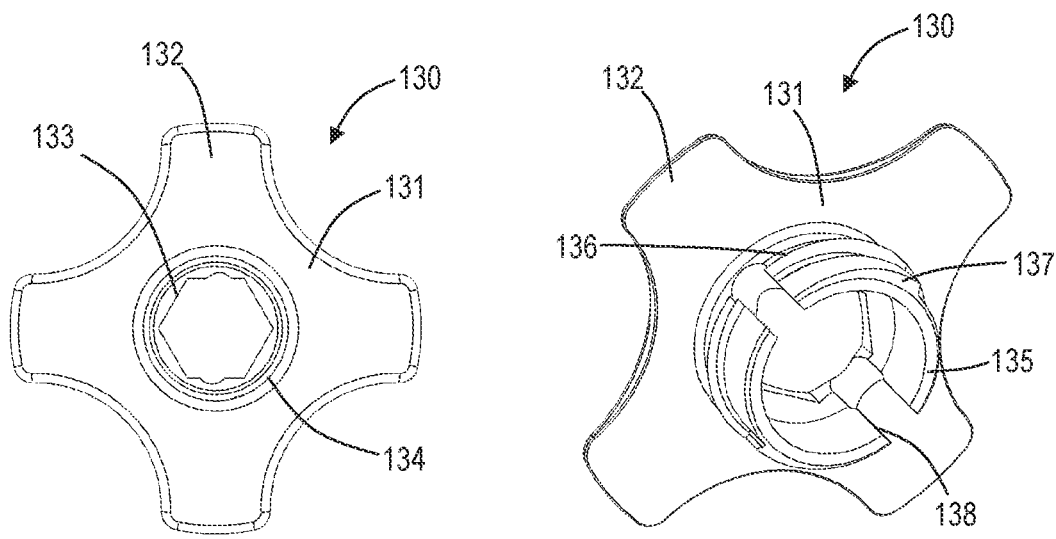
FIG. 8 is a top view of the retention cap of FIG. 7.
FIG. 9 is a bottom perspective view of the retention cap of FIGS. 7-8.
Figure 10:
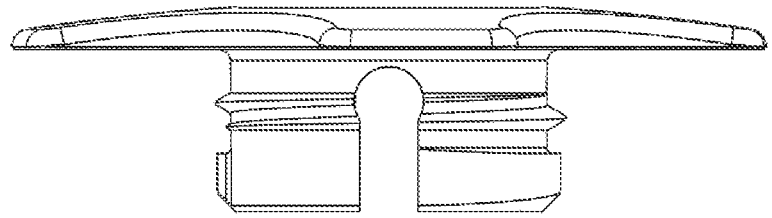
FIG. 10 is a side view of the retention cap of FIGS. 7-9.

FIGS. 1-23 illustrate one exemplary embodiment of the lumbar plate system 100 of the present disclosure. Referring to FIGS. 1 and 2, the lumbar plate system 100 includes a lumbar plate 110, one or more retention caps 130, and bone screws 150. In the embodiment illustrated in FIGS. 1 and 2, the lumbar plate system 100 includes a centrally located retention cap 130 for securing the bone screws 150 in place relative to the lumbar plate 110.

FIGS. 3-6 illustrate the lumbar plate 110 of the exemplary embodiment of the lumbar plate system 100. Referring to FIGS. 3-6, in the embodiment illustrated, the lumbar plate 110 incudes a sagittal profile that is symmetric about the transverse and coronal planes. The lumbar plate 110 includes screw holes 114 formed in a body 112 thereof. In embodiments, the screw holes 114 consist of four poly-axial screw holes with angulation of 0°-20°. The screw holes 114 are positioned on an appropriately sized bolt-pattern relative to the central axis of the lumbar plate 110. In embodiments, the screw hole bolt pattern size is optimized to ensure integrity of the lumbar plate 110, enable surgical bone screw preparation, and reduce instances of screw contact interference between contiguous interbody levels with the same system. In embodiments, the lumbar plate 110 is a metallic plate formed of a biocompatible material.

Bone-interfacing surfaces 116 at a bottom of the lumbar plate 110 are concave and are adapted to conform to the typical anatomy of the lateral thoracolumbar vertebral bodies. Instrument-mating convex surfaces of the lumbar plate 110 are optimized for minimal plate thickness. Plate edges and transitions 118 are minimized to prevent soft-tissue irritation. In embodiments, the body 112 includes a shoulder 117 around the top edge thereof and the top surface 15 is recessed relative to the shoulder 117. With this configuration, the head of the retention cap 130 can be inset and at least partially recessed relative to the shoulder 117, while the retention cap 130 is coupled to the lumbar plate 110.

The lumbar plate 110 includes a locking feature 120. In the embodiment illustrated, the locking feature 120 is a central internal locking feature including from lateral-to-medial: an internal thread 122, a blind recess bore 124, and a clocking star-pattern 126.

The internal thread 122 includes a lead-in surface 123 that is chamfered about a pre-drill hole to enable system assembly with the retention cap 130. The thread size of the internal thread 122 defines the size and shape of the blind recess bore 124 and clocking-star pattern 126. The thread major diameter and pitch diameter are traditional according to machinist guidelines. However, in embodiments, the minor diameter is increased to optimize the interface with the retention cap 130.

The blind recess bore 124 is below the internal thread lead-in surface 123 by a distance equal to at least one thread pitch. This distance ensures at least one thread is within the central hole 121 of the lumbar plate 110 defined by the locking feature 120. The major diameter of the blind recess bore 124 is equal to, or greater than the major diameter of the internal thread 122 but the difference is minimized. The top and bottom vertices of the blind recess bore 124 are chamfered equivalent to the thread-form angle (i.e., typically) 60°.

The clocking star-pattern 126 is below the blind recess bore 124. The height of the clocking-star pattern 126 is optimized and adapted for mechanism functional integrity. The clocking star-pattern 126 is defined by axially symmetric cut-outs 127 spaced evenly about an axis 360-degree of rotation of the central hole 121. The position of the cut-outs 127 can be optimized for preferred rotational control at defined angular intervals (i.e., factors of 360). The extent of the cut-outs 127 major diameter is optimized relative to the minor diameter of the central hole 121, the central hole 121 being a through hole. However, the major diameter of the cut-outs 127 is coincident with the major diameter of the blind recess bore 124. The cut-out geometry transitions from the major diameter thereof to the minor diameter of the central hole 121, which is equivalent to the modified minor diameter of the internal thread 122.

FIGS. 7-10 illustrate the retention cap 130 of the exemplary embodiment of the lumbar plate system 100. Referring to FIGS. 7-10, the retention cap 130 includes a head 131 and a shank 135. In embodiments, the retention cap 130 is formed of metal. The head 131 is scalloped at 90-degree intervals about a central axis of the retention cap 130 forming tangs 132. In the embodiment illustrated, the head includes four tangs 132 or tabs (one for each screw hole 114 of the lumbar plate 110).

The shank 135 includes an external thread 136, two or more protrusions 137, and relief cut-outs 138. The external thread 136 is adapted to mate with the internal thread 122 of the lumbar plate 110. The external thread 136 is of minimal height (i.e., turns) and modified major outer diameter. The major diameter of the external thread 136 may be increased or decreased depending on the system manufacturing assembly method. In embodiments, the two or more protrusions are teeth, symmetric, and evenly spaced about the central axis 360-degree of rotation (i.e., factors of 360) of the shank 135.

The relief cut-outs 138 are orthogonal to the central axis of the shank 135, extending from an end of the shank 135 towards the head 132. The size and height of the relief cut-outs 138 is such to allow the shank 135 to deflect inward when compressing the two or more protrusions 137. The relief cut-outs 138 are clocked relative to the two or more protrusions, such as at 90° or half the angular distance between the protrusions.

The retention cap 130 includes a screw drive 133 formed therein. In embodiments, the screw drive 133 is one of a slotted drive, a cruciform drive, a square drive, an internal hex drive, and the like. The screw drive 133 can be formed in the head 131, the shank 135, or a combination thereof. In the embodiment illustrated, the screw drive 133 includes a female cut-out that interfaces with a driver instrument and is recessed in a counter-bore hole 134 formed in head 131. The counter-bore hole 134 creates a shoulder about the screw drive 133 and acts as a mechanical stop for which surgical instrumentation (i.e., hex driver, screwdriver, and the like) can interface. In embodiments, the female cut-out of the screw drive 133 extends at least partially through the long axis of the shank 135.

Figure 11:
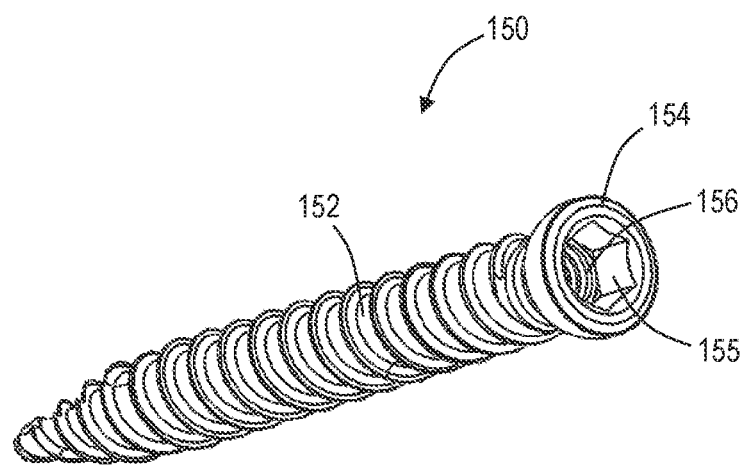
FIG. 11 is a perspective view of a bone screw of the lumbar plate system of FIGS. 1 and 2.
Figure 12:
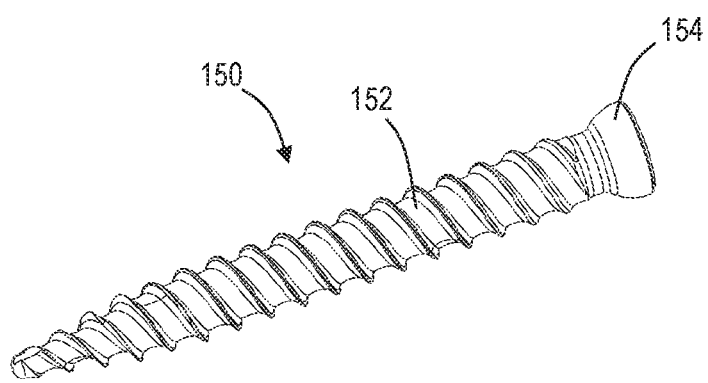
FIG. 12 is a side view of the bone screw of FIG. 11.
Figure 13:
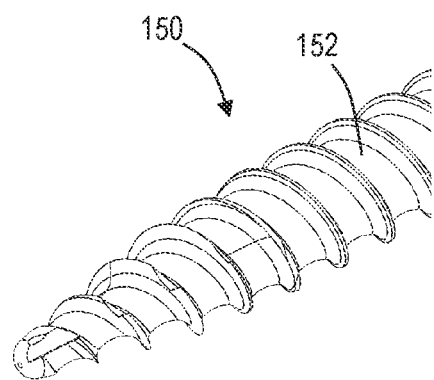
FIG. 13 is a perspective view of a tip of the bone screw of FIGS. 11-12.

FIGS. 11-13 illustrate a bone screw 150 of the exemplary embodiment of the lumbar plate system 100. Referring to FIGS. 11-13, the bone screws 150 are metallic poly-axial screws. In embodiments, the bone screws 150 are thoracolumbar bone screws of varying overall length and major diameter appropriate for interface with the screw holes 114 of the lumbar plate 110. In embodiments, the screw head 154 is convex semi-spherical to enable multiple axis of insertion with the concave semi-spherical screw holes 114 of the lumbar plate 110. However, other types and styles of bone screws can also be used.

Figure 14:
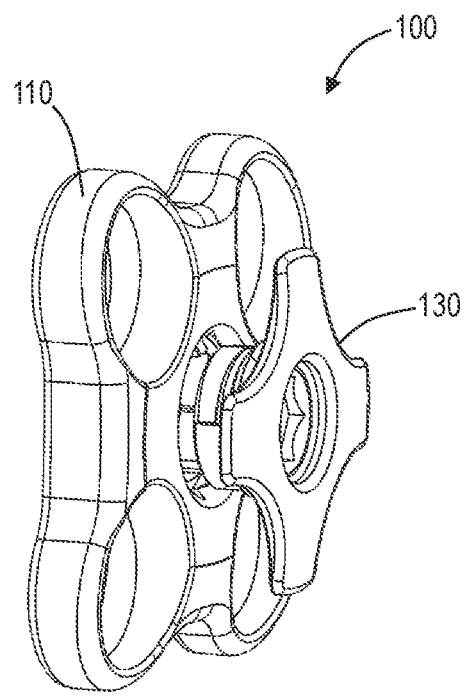
FIG. 14 is a perspective view of the lumbar plate system of FIGS. 1 and 2 illustrating an initial insertion of the retention cap into the lumbar plate.
Figure 15:
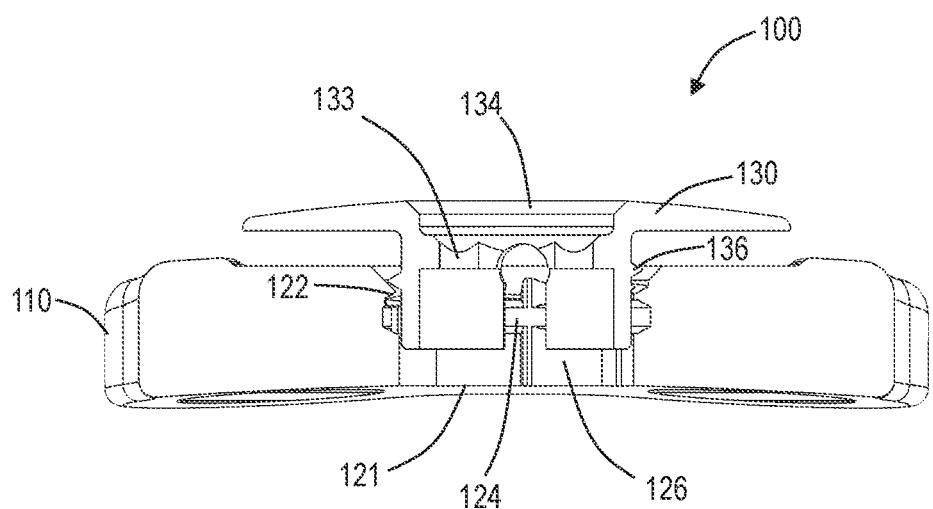
FIG. 15 is a cross-sectional view of the lumbar plate system of FIG. 14 illustrating the initial insertion of the retention cap into the lumbar plate.
Figure 16:
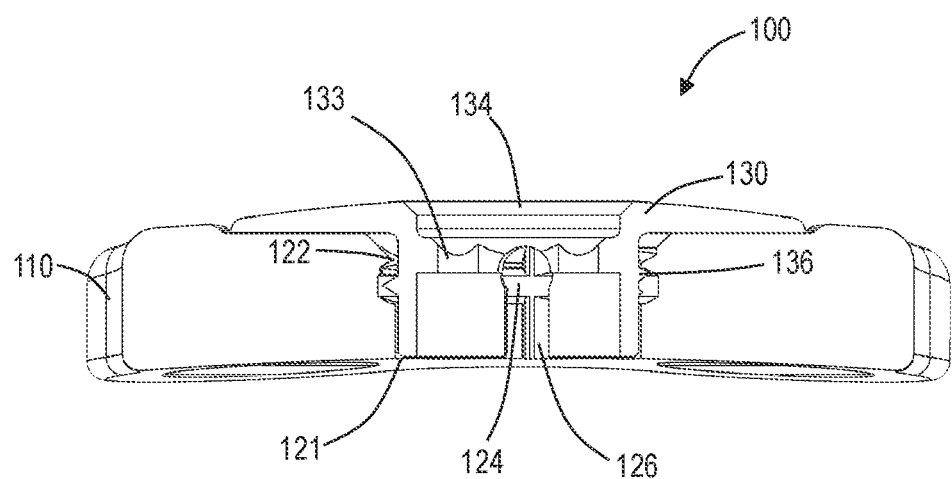
FIG. 16 is a perspective view of the lumbar plate system of FIGS. 1 and 2 illustrating a thread of the retention cap recessed into a bore hole of the lumbar plate.
Figure 17:
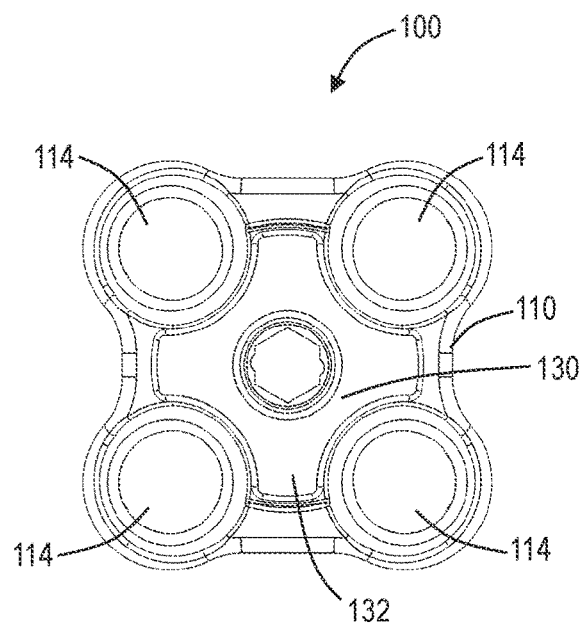
FIG. 17 is a top view of the lumbar plate system of FIGS. 1 and 2 illustrating the retention cap in an unlocked position in the lumbar plate.
Figure 18:
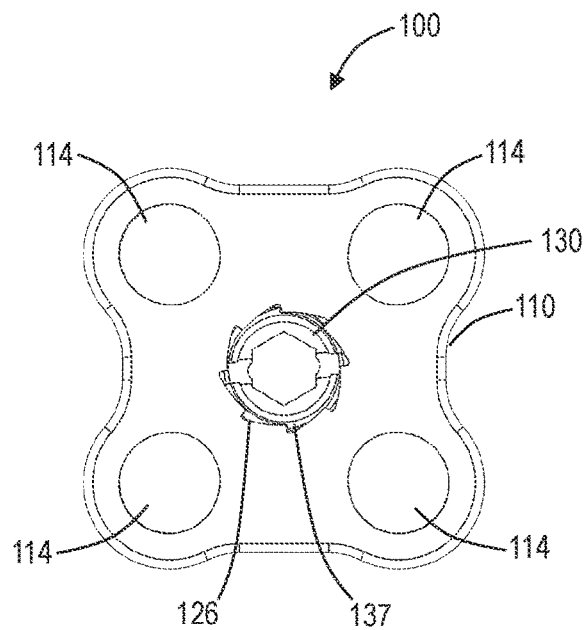
FIG. 18 is a bottom view of the lumbar plate system of FIGS. 1 and 2 illustrating the retention cap in an unlocked position in the lumbar plate.
Figure 19:
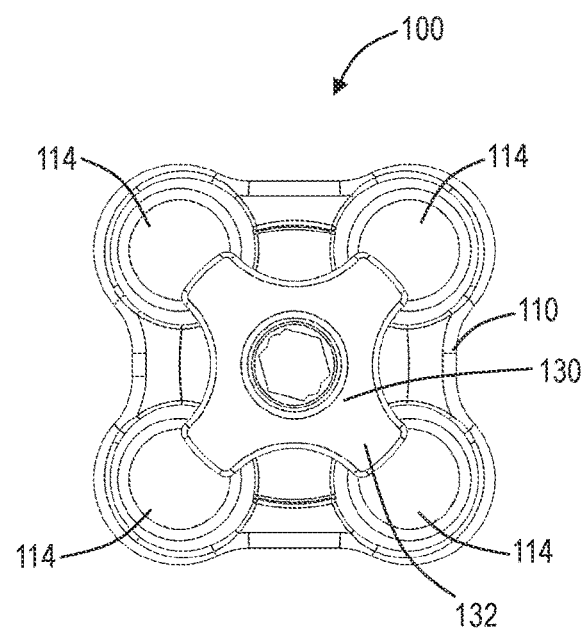
FIG. 19 is a top view of the lumbar plate system of FIGS. 1 and 2 illustrating the retention cap in a locked position in the lumbar plate.
Figure 20:
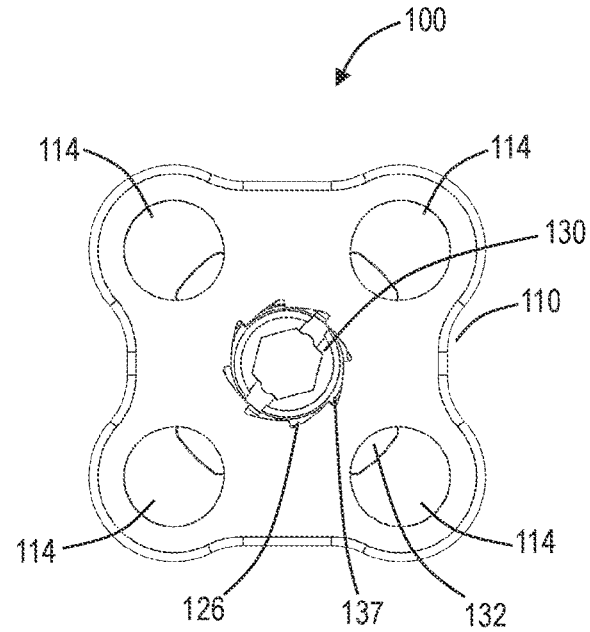
FIG. 20 is a bottom view of the lumbar plate system of FIGS. 1 and 2 illustrating the retention cap in a locked position in the lumbar plate.

FIGS. 14-16 illustrate assembly of the lumbar plate system 100. In embodiments, the retention cap 130 assembles to the lumbar plate 110 during manufacturing and prior to surgical usage. Referring to FIGS. 14-16, first, the two or more protrusions 137 of the retention cap 130 are inserted into the matching clocking star-pattern 126 of the lumbar plate 110 until the external thread 136 of the retention cap 130 dead-stops against the internal thread 122 of the lumbar plate 110. The two or more protrusions 137 have an external minor diameter slightly greater (i.e., slip-fit interference) than an internal minor diameter of the clocking star-pattern 126. The external minor diameter of the two or more protrusions 137 will interfere with the internal minor diameter of the clocking star-pattern 126 prior to the dead-stopping of the external thread 136 of the retention cap 130. The initial insertion of the retention cap 130 into the lumbar plate 110 until the dead-stop of the external thread 136 on the internal thread 122 is illustrated in FIGS. 14 and 15.

Next, the retention cap 130 is rotated clockwise to engage with the central hole 121. During rotation, and as the shank 135 of the retention cap 130 travels axially into the central hole 121 of the lumbar plate 110, the two or more protrusions 137 will deflect and release with the cut-outs 126 of the clocking star-pattern 126. After successful thread-rotation, the thread engagement is relieved when the external thread 136 of the retention cap 130 recedes into the blind recess bore 124 of the lumbar plate 110, which is below the internal thread 122 of the lumbar plate 110. There is minimal clearance between the major diameter of the external thread 136 and the internal major diameter of the blind recess bore 124. In embodiments, line-to-line contact is acceptable.

In embodiments, the blind recess bore 124, and in combination with the dimensions of the position of the external thread 136 of the retention cap along the shank 135 of the retention cap 130 relative the thread depth of the internal thread 122 of the lumbar plate 110, is adapted to enable application of axial compression to the retention cap 130 with the lumbar plate 110. This is due to the external thread 136 interfacing with the blind recess bore 124, and in particular, a proximal chamfer surface of the blind recess bore 124 opposing the external thread 136. In embodiments, this interference relationship prevents the retention cap 130 from axial travel, or displacement, during clockwise rotation thereof. FIG. 16 illustrates the external thread 136 being recessed into the blind recess bore 124.

FIGS. 17-23 illustrate the usage and function of the lumbar plate system 100. Referring to FIGS. 17-20, in an assembled and unlocked state, the tangs 132 of the retention cap 130 are positioned between the screw holes 114 of the lumbar plate 110. The scallops of the head 132 align with the screw holes 114 and appear concentric with the screw holes 114. In a locked state, the tangs 132 of the retention cap 130 are positioned at least partially over the screw holes 114 of the lumbar plate 110.

Figure 21:
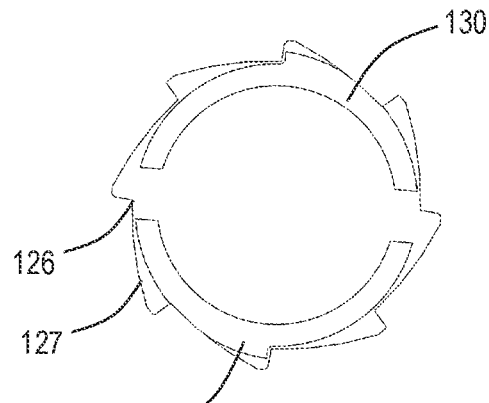
FIG. 21 illustrates a radial interference between a shank of the retention cap and a cut-out of the lumbar plate while the retention cap is in the unlocked state.
Figure 22:
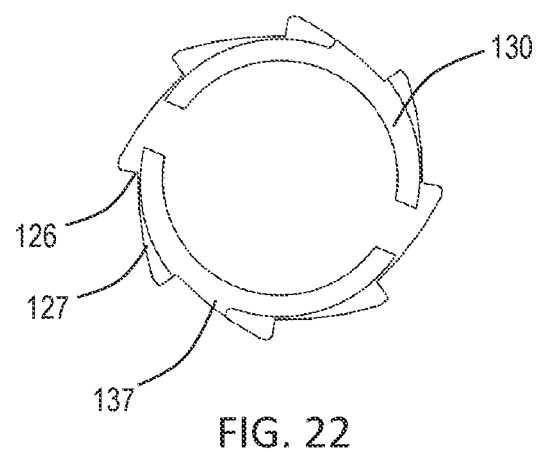
FIG. 22 illustrates a radial interference between a shank of the retention cap and a cut-out of the lumbar plate while the retention cap is in an intermediate state.
Figure 23:
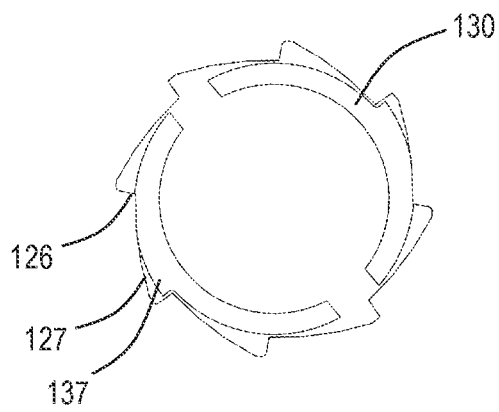
FIG. 23 illustrates a radial interference between a shank of the retention cap and a cut-out of the lumbar plate while the retention cap is in the locked state.

Referring to FIGS. 21-23, the configuration of the clocking star-pattern 126 and the two or more protrusions 137 is adapted to control axial rotation of the retention cap 130 relative to the lumbar plate 110, and in particular about a central axis of the central hole 121. During rotation, the two or more protrusions 137 deflect the shank 135 of the retention cap 130 due to increasing rotational interference between the cut-outs 127 of the clocking star-pattern 126.

In the embodiment illustrated, the retention cap 130 rotates only in one direction after assembly of the retention cap 130 to the lumbar plate 110. In particular, the protrusions 137 interface with the cut-outs 127 of the clocking star-pattern 126 to prevent rotation in an opposing direction by a hard-mechanical stop defined by the cut-outs 127 and the two or more protrusions 137. This configuration is adapted to permit rotation of the retention cap 130 in the threading direction and to oppose rotation in the opposing direction (the unthreading direction). Thus, the protrusions 137 and the clocking star-pattern 126 are adapted such that the functional rotation for rotating the retention cap 130 between the unlocked and lock states is in the rotational direction that matches the thread rotation used for assembling the retention cap 130 to the lumbar plate 110. Because the retention cap 130 cannot rotate in the opposing direction, the retention cap 130 cannot disassemble by means of the previously aforementioned thread-engagement.

In embodiments, the threading direction is right-handed (clockwise) and the protrusions 137 and the clocking star-pattern 126 are adapted to permit rotation in the right-handed direction and to oppose rotation in the left-handed (counterclockwise) direction. However, in other embodiments, the lumbar plate system 100 is in a left-handed configuration for the threading and functional rotation of the retention cap 130 and the right-handed rotation thereof is opposed by the configuration of the protrusions 137 and the clocking star-pattern 126.

The retention cap 130 does not freely rotate in the one direction when assembled with the lumbar plate 110. The two or more protrusions 137 have external minor diameter slightly greater than (i.e., slip-fit interference) the internal minor diameter of the clocking star-pattern 126. Surface interference between the components provides resistance to rotation of the cap in the one direction.

The major diameter of the two or more protrusions 137 is less than the major internal diameter of the cut-outs 127 of the clocking star-pattern 126. This ensures the shank 132 of the retention cap 130 can release when the position of the two or more protrusions 137 aligns with the cut-outs 127 of the clocking star-pattern 126.

From a lateral surgical approach, the surgeon will slide the lumbar plate system 100 down a central shaft instrument, or K-wire, that is inserted into the intervertebral space. The lumbar plate 110 is positioned relative to the vertebrae. The surgeon uses instrumentation to prepare the bone for the bone screws 150. The surgeon drives the bone screws 150 through the screw holes 114 of the lumbar plate 110 in an alternating 1-3-2-4 pattern. After all bone screws 150 are seated within the screw holes 114, the surgeon will rotate the retention cap 130 to the desired position with the tangs 132 overlapping the head 154 of each of the bone screws 150. The retention cap 130 will overhang the screw holes 114 to ensure the bone screws 150 cannot back-out.

During revision surgery, the retention cap 130 can be rotated until the tangs 132 do not obstruct the screw holes 114. Then the bone screws 150 can be removed, and finally the lumbar plate system 100 is removed.

Figure 24:
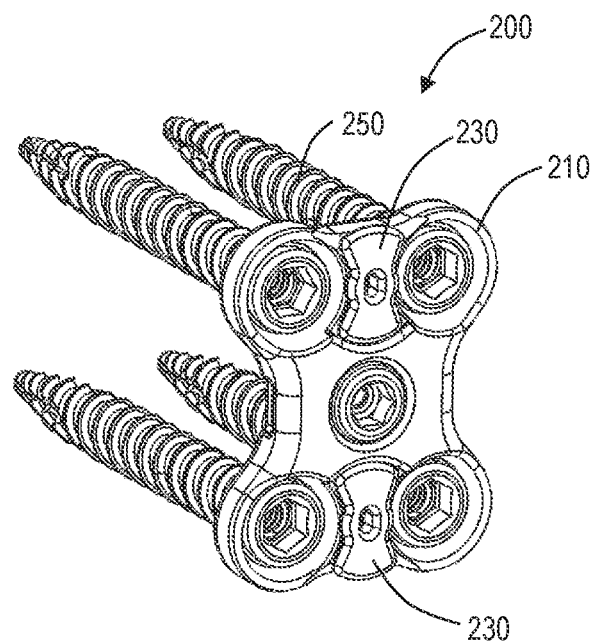
FIG. 24 is a perspective view of another exemplary embodiment of the lumbar plate system of the present disclosure in an unlocked state.
Figure 25:
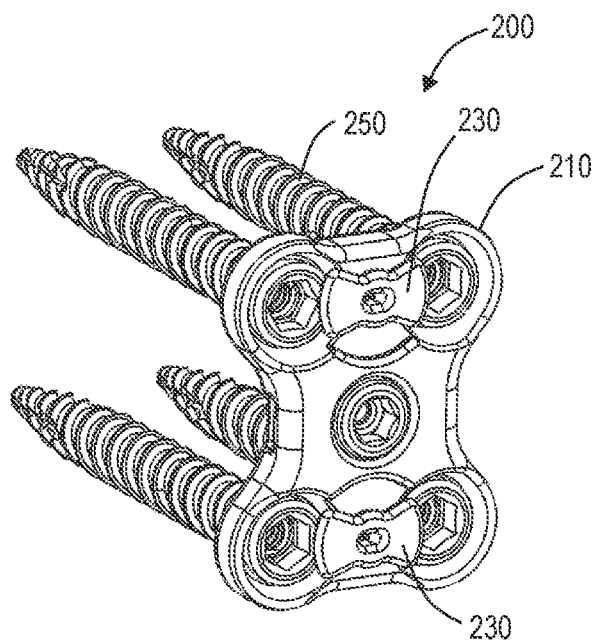
FIG. 25 is a perspective view of the lumbar plate system of FIG. 24 in a locked state.
Figure 26:
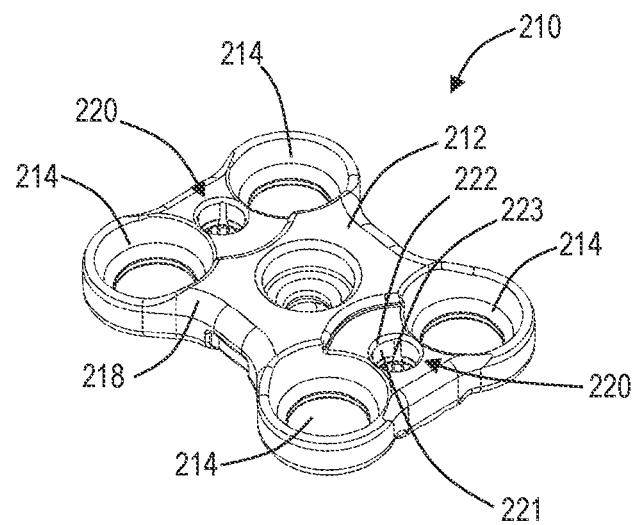
FIG. 26 is a perspective view of the lumbar plate of the lumbar plate system of FIGS. 24 and 25.
Figure 27:
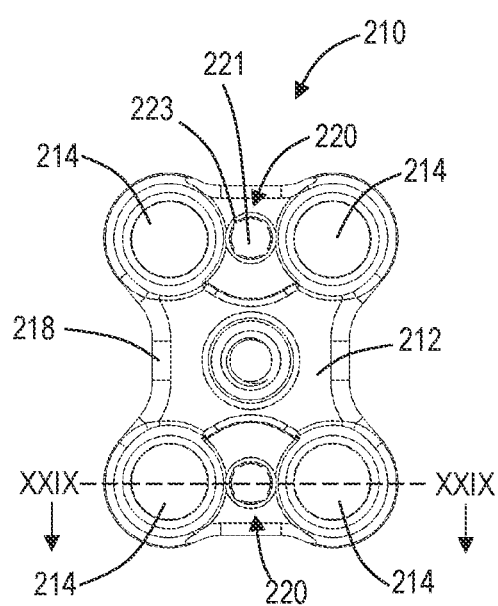
FIG. 27 is a top view of the lumbar plate of FIG. 26.
Figure 28:
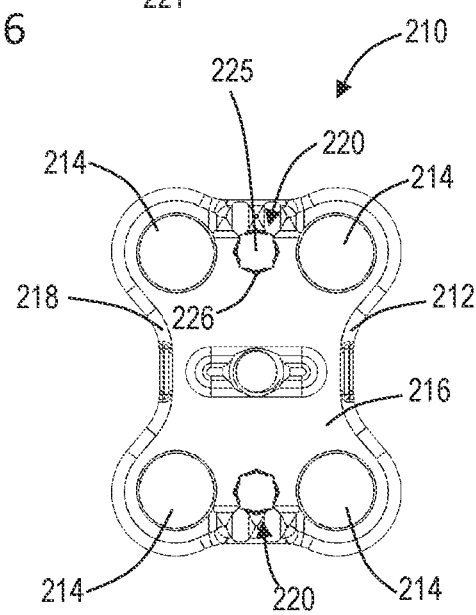
FIG. 28 is a bottom view of the lumbar plate of FIGS. 26-27.
Figure 29:
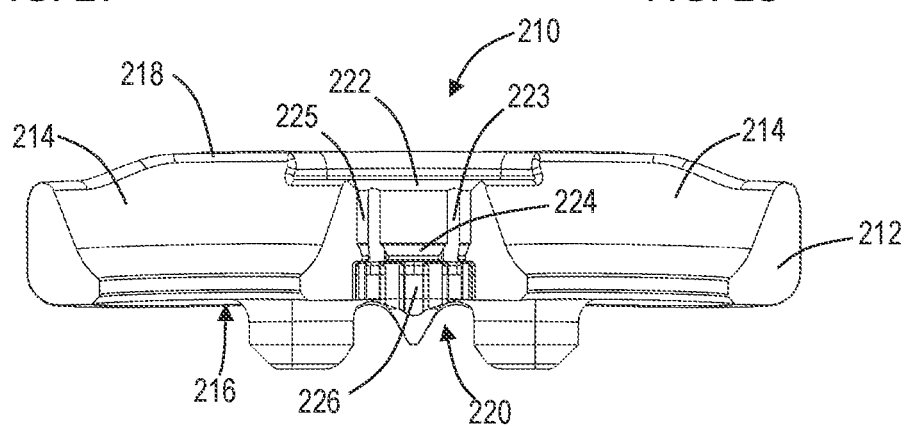
FIG. 29 is a cross-sectional view of the lumbar plate of FIGS. 26-28 taken along the line XXIX-XXIX in FIG. 27.
Figure 30:
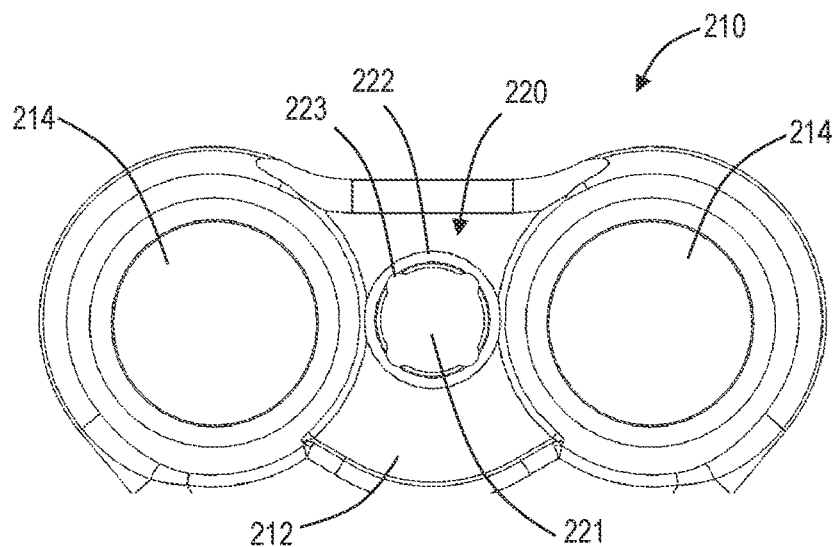
FIG. 30 is a detail top perspective of the lumbar plate of FIGS. 26-29.
Figure 31:
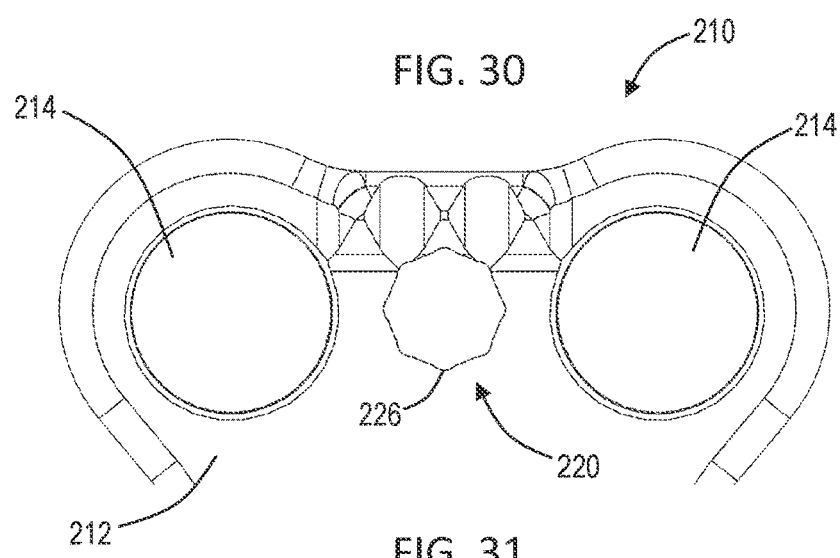
FIG. 31 is a detail bottom perspective of the lumbar plate of FIGS. 26-30.
Figure 32:
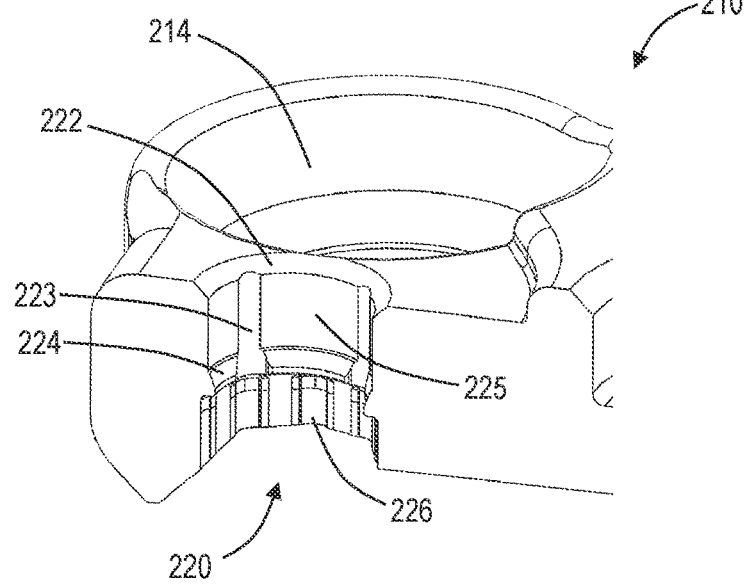
FIG. 32 is a cross-section of a perspective view of the lumbar plate of FIGS. 26-31.
Figure 33:
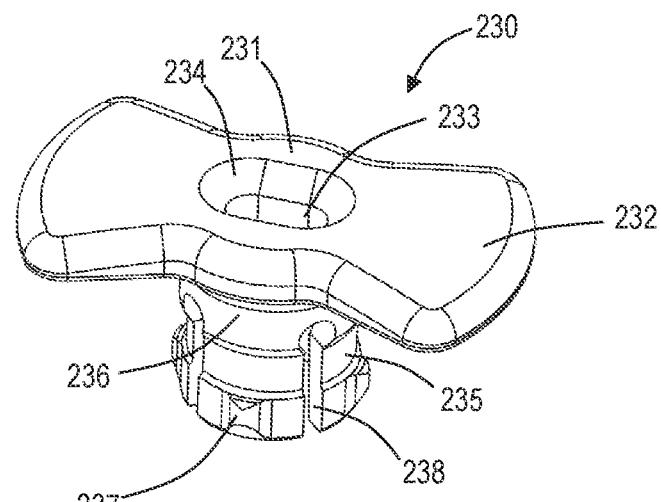
FIG. 33 is a perspective view of the retention cap of the lumbar plate system of FIGS. 24 and 25.
Figure 34:
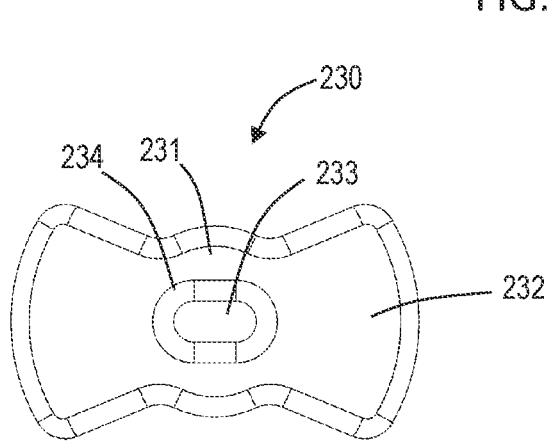
FIG. 34 is a top view of the retention cap of FIG. 33.
Figure 35:
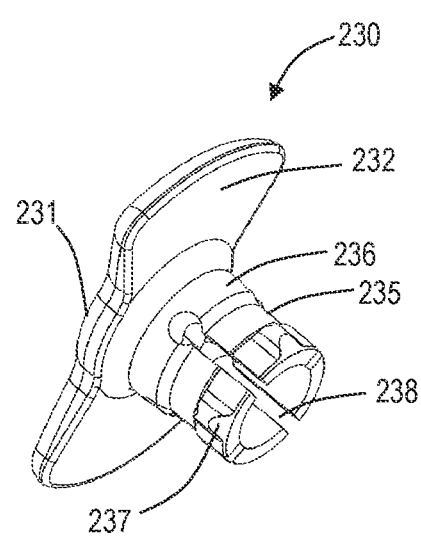
FIG. 35 is a bottom perspective view of the retention cap of FIGS. 33-34.
Figure 36:
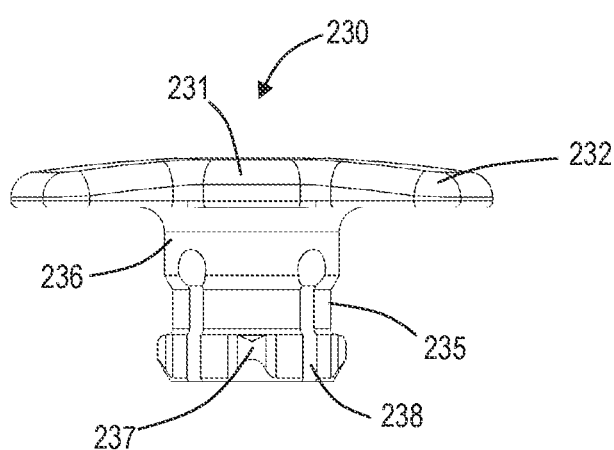
FIG. 36 is a side view of the retention cap of FIGS. 33-35.
Figure 37:
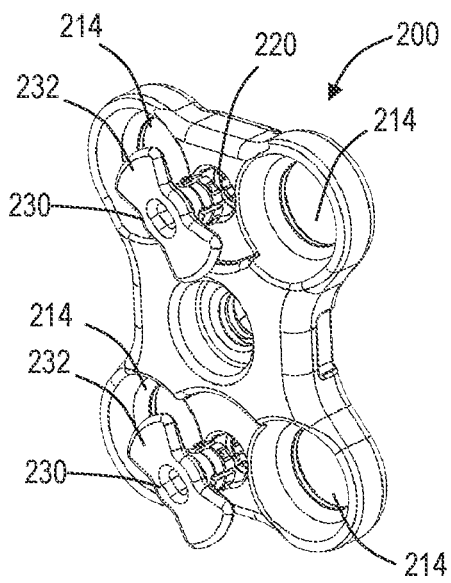
FIG. 37 is a perspective view of the lumbar plate system of FIGS. 24 and 25 illustrating an initial insertion of the retention caps into the lumbar plate.
Figure 38:
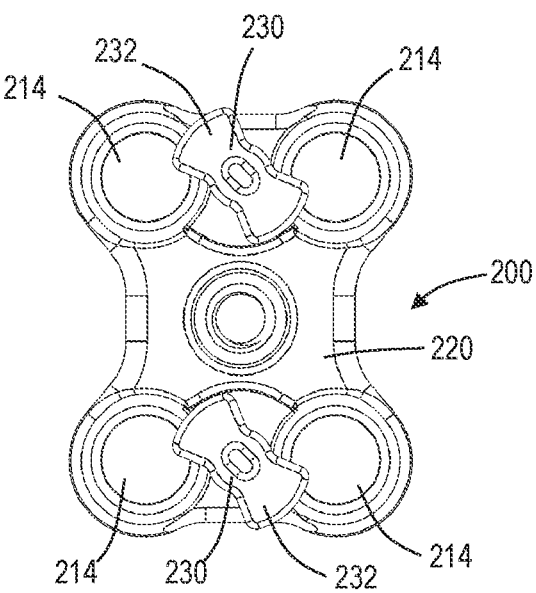
FIG. 38 is a top view of the lumbar plate system of FIG. 37 illustrating the initial insertion of the retention caps into the lumbar plate.
Figure 39:
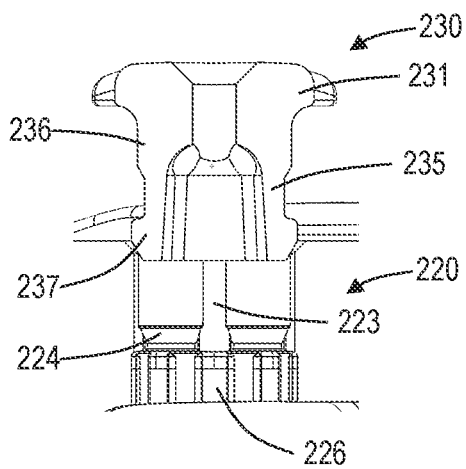
FIG. 39 is a cross-sectional view of a portion the lumbar plate system of FIGS. 37 and 38 illustrating the initial insertion of a retention cap into the lumbar plate.
Figure 40:
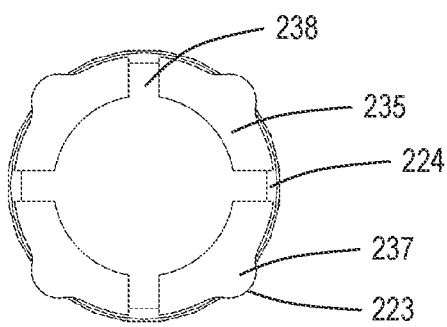
FIG. 40 is a cross-sectional view of the protrusions in an interference condition with the insertion-assembly slots during assembly of the retention cap to the lumbar plate.

FIGS. 24-42 illustrate another exemplary embodiment of the lumbar plate system 200 of the present disclosure. Referring to FIGS. 24 and 25, the lumbar plate system 200 includes a lumbar plate 210, one or more retention caps 230, and bone screws 250. In the embodiment illustrated in FIGS. 24 and 25, the lumbar plate system 200 includes two retention caps 230 for securing the bone screws 250 in place relative to the lumbar plate 210.

FIGS. 26-32 illustrate the lumbar plate 210 of the lumbar plate system 200. Referring to FIGS. 26-32, in the embodiment illustrated, the lumbar plate 210 incudes screw holes 214 formed in a body 212 thereof. In embodiments, the screw holes 214 consist of four poly-axial screw holes, such as the screw holes 114 described above. In embodiments, the lumbar plate 210 is a metallic plate formed of a biocompatible material.

The bone-interfacing surfaces 216 at a bottom of the lumbar plate 210 are concave and conform to the typical anatomy of the lateral thoracolumbar vertebral bodies. In embodiments, protrusions, such as pyramid shaped protrusions, symmetric about the transverse and coronal plane, minimize plate micromotion during surgical placement against bone. The lumbar plate 210 exhibits two detents in the transverse plane and symmetric about the sagittal plane for mating with instrumentation. Plate edges and transitions 218 are minimized to prevent soft-tissue irritation.

The lumbar plate 210 includes two locking features 220. Each of the locking features 220 includes a cut-out or a hole 221 located on a coronal plane of the lumbar plate 210. In the embodiment illustrated, the two locking features 220 are symmetric about the transverse plane. Each locking feature 220 includes several internal features intended to mate with a retention cap 230: a lead-in chamfer 222, insertion-assembly slots 223, a proximal self-centering diametric interference shoulder 225, blind interference ribs 224, and relief detents 226. In the embodiment illustrated, each of the features are equal-spaced every 90° about a central axis of the locking feature 220.

The lead-in chamfer 222 is chamfered edge adapted to co-axially align the retention cap 230 with the locking feature 220. The lead-in chamfer 222 is also sized and adapted to introduce initial inward flexion to the shank 235 of the retention cap 230 described in detail below.

In the embodiment illustrated, there are four insertion-assembly slots 223. The insertion-assembly slots 223 are female features that extend from the lead-in chamfer towards a bottom of the lumbar plate 210. The insertion-assembly slots 223 are adapted to mate with protrusions 237, such as male detents, of the retention cap 230 described below. The mating relationship is a slight press-fit to induce inward flexion into the shank 235 along the overall length thereof. The insertion-assembly slots 223 are clocked and rotationally offset from the relief detents 226. In the embodiment illustrated, the insertion-assembly slots 223 are clocked 45° from the rotational-alignment relief detents 226.

The proximal diametric shoulder 225 is adapted to form a slip-fit condition with a proximal shoulder 236 of the retention cap 230 underneath its head. This feature self-centers and locates the two components during assembly, provides some rotational stability and control, and improves disassembly resistance.

The blind interference ribs 224 are adapted to overhang the protrusions 237 of the retention cap 230 to prevent the construct axial disassembly via a snap relief mechanism. In the embodiment illustrated, the lumbar plate 210 includes four blind interference ribs 224 that circumferentially span between the insertion-assembly slots 223. Further, in the embodiment illustrated, the blind interference ribs 224 are positioned at an end of the insertion-assembly slots 223 distal to the lead-in chamfer 222.

The relief detents 226 are rotational-alignment female relief detents positioned underneath the blind interference ribs 224. The relief detents 226 are axially extending slots adapted to capture the detents of protrusions 237 (described in detail below) of the retention cap 230 for rotational alignment thereof. The relief detents 226 and protrusions 236 mate via a line-to-line condition. The inner diameter between the slots of detents 226 is smaller than the outer diameter of the protrusions 237 of the retention cap 230 to illicit interference and to prevent rotational freedom.

In the embodiment illustrated, the insertion-assembly slots 223 each align (circumferentially) with a relief detent 226 allowing the insertion-assembly slots 223 to guide the protrusions 236 axially towards the associated relief detents 226 during assembly.

FIGS. 33-36 illustrate the retention cap 230 of the lumbar plate system 200. Referring to FIGS. 33-36, the retention cap 230 includes a head 231 and a shank 235. In embodiments, the retention cap 230 is formed of metal. In embodiments, the head 231 includes a bilateral profile to maximize or minimize exposure based on the functional rotational alignment of the retention cap 230. A thickness of the head 231 is adapted to prevent deflection thereof to prevent screw back-out when the lumbar plate system 200 is in a locked state. In the embodiment illustrated, the head 231 does not extend beyond the overall thickness of the lumbar plate 210 when assembled thereto.

The head 231 includes tangs 232 or tabs (one for each screw hole 214 of the lumbar plate 210 that will be covered by the retention cap 230 when in a locked state). In the embodiment illustrated, the head 231 includes two tangs and includes a bowtie like shape. In embodiments, the profile shape of the tangs 232 is optimized for maximum coverage of the head of the bone screw 250 when the lumbar plate 200 is in a locked state.

The retention cap 230 also includes a screw drive 233 formed therein. In embodiments, the screw drive 233 is one of a slotted drive, a cruciform drive, a square drive, an internal hex drive, and the like. The screw drive 233 can be formed in the head 231, the shank 235, or a combination thereof. In the embodiment illustrated, the screw drive 233 includes a female cut-out that interfaces with a driver instrument and is recessed in a counter-bore hole 234 formed in head 231. The counter-bore hole 234 creates a shoulder about the screw drive 233 and acts as a mechanical stop for which surgical instrumentation (i.e., hex driver, screwdriver, and the like) can interface. In embodiments, the female cut-out of the screw drive 233 extends at least partially through the long axis of the shank 235.

The shank 235 is positioned below the head 231. The shank 235 includes a shoulder 236, protrusions 237, and relief cut-outs 238. The shoulder 236 is proximal to the head 231 and generally includes a cylindrical shape. The protrusions 237 are male detents that protrude radially outward and are positioned at a distal end of the shank 235 relative to the head 231 and the shoulder 236. In the embodiment illustrated, the shank includes four protrusions 237 that are clocked at 90° about a central axis of the shank 235.

The relief cut-outs 238 are orthogonal to the central axis of the shank 235, extending from an end of the shank 235 towards the head 232. In the embodiment illustrated, the relief cut-outs 238 extend partially into the shoulder 236. The size and height of the relief cut-outs 238 is such to allow the shank 235 to deflect inward when compressing the protrusions 237. The relief cut-outs 238 are clocked relative to the protrusions 237, such as at 45° or half the angular distance between the protrusions 238. In the embodiment illustrated, the shank 235 includes four relief cut-outs 238.

The shank 235 also includes an internal bore extending therethrough, such that the shank 235 generally includes one of a hollow conical frustrum shape and a hollow cylinder shape. This shape, along with the relief cut-outs 238 and an appropriate amount of wall thickness ensures that the resulting tabs formed thereby will deflect when an appropriate amount of force is applied but is generally adapted to resist deflection to prevent unwanted rotation of the retention cap 230. In embodiments, the conical shape of the bore modulates the wall thickness of the shank 235 to optimize stress distribution during inward flexion of the protrusions 237.

FIGS. 37-42 illustrate assembly of the lumbar plate system 200. In embodiments, each retention cap 230 assembles to the lumbar plate 210 during manufacturing and prior to surgical usage. Referring to FIGS. 37-42, First, protrusions 237 are aligned with the insertion-assembly slots 223. In the embodiment illustrated, the longest cross-section plane of the bilateral profile of the retention cap 230 is oriented approximately 45° relative to the coronal plane of the lumbar plate 210 at this stage.

Under downward force, the retention cap 230 is pressed co-axially into the hole 221 where the tabs of the shank 235 flex inward (i.e., conical) due to the proximal press-fit condition between the female insertion-assembly slots 223 and male protrusions 237.

As the protrusions 237 slide along the insertion-assembly slots 223, the shoulder 236 of the shank 235 interfaces with the proximal diametric shoulder 225 of the hole 221.

Figure 41:
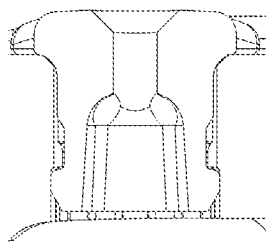
FIG. 41 is a cross-sectional view of a portion the lumbar plate system of FIGS. 24 and 25 illustrating the completed insertion of a retention cap into the lumbar plate.
Figure 42:
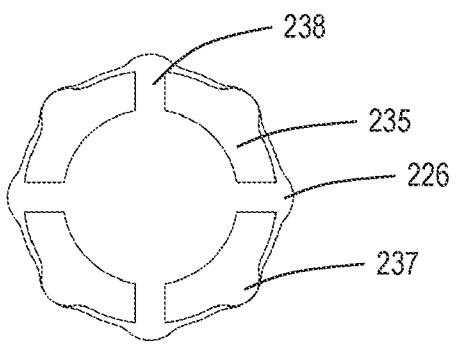
FIG. 42 is a cross-sectional view of the protrusions in an interference condition with the relief detents that circumferentially align with the insertion-assembly slots upon insertion of the retention cap into the lumbar plate.

As illustrated in FIG. 41, when an underside of the head 231 contacts the surface of the lumbar plate 210 proximal to the hole 221, the protrusions 237 snap below the blind interference ribs 224 and expand outward into the relief detents 226 circumferentially aligned with the insertion-assembly slots 223 (i.e., snap mechanism).

Each retention cap 230 is rotated 45° to an assembly position using a driver instrument. In this rotational alignment, the protrusions 237 are rotated to another set of relief detents 226, clocked relative to the relief detents aligned with the insertion-assembly slots 223 and are contained by the holes four blind interference ribs 224.

Figure 43:
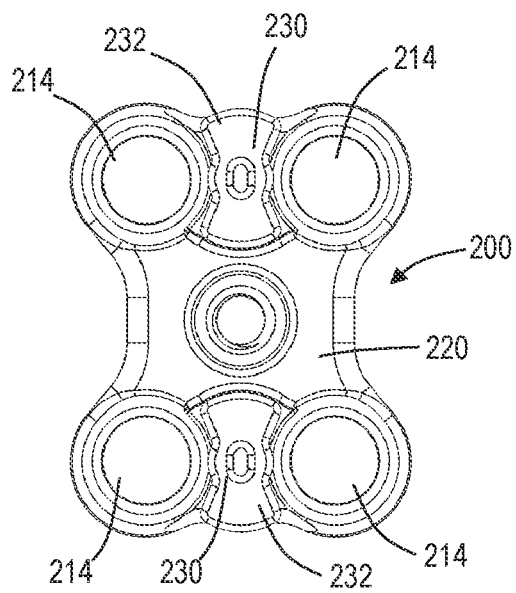
FIG. 43 is a top view of the lumbar plate system of FIGS. 24 and 25 illustrating the retention caps in an unlocked position in the lumbar plate.
Figure 44:
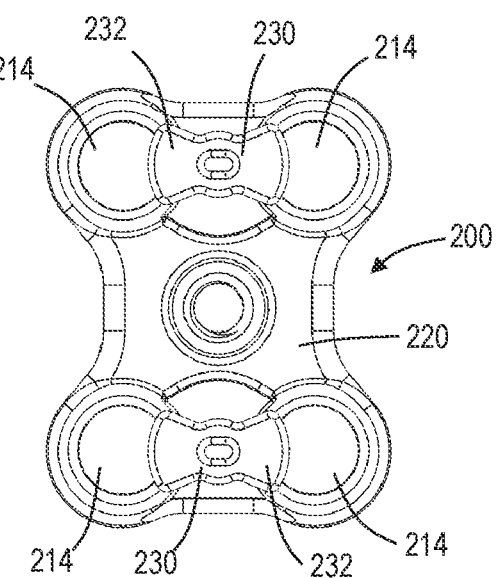
FIG. 44 is a top view of the lumbar plate system of FIGS. 24 and 25 illustrating the retention caps in a locked position in the lumbar plate.
Figure 45:
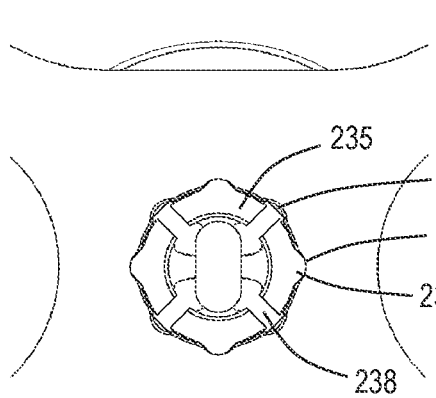
FIG. 45 illustrates a radial interference between the protrusions of the retention cap and relief detents of the lumbar plate while the retention cap is in the unlocked state.
Figure 46:
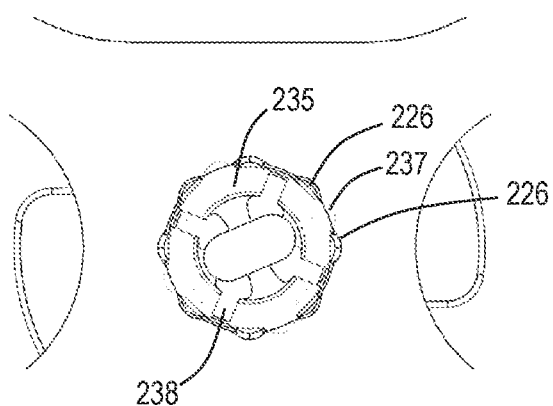
FIG. 46 illustrates a radial interference between the protrusions of the retention cap and relief detents of the lumbar plate while the retention cap is in an intermediate state.
Figure 47:
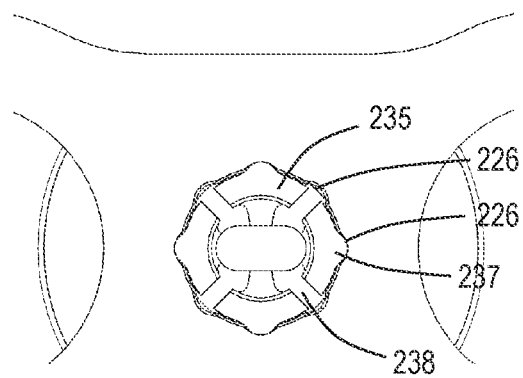
FIG. 47 illustrates a radial interference between the protrusions of the retention cap and relief detents of the lumbar plate while the retention cap is in the locked state.

FIGS. 43-47 illustrate the usage and function of the lumbar plate system 100. Referring to FIGS. 43-47, in an assembled and unlocked state, the tangs 232 of the retention cap 230 are positioned between screw holes 214 so as to not axially overlap with the screw holes 214 as illustrated in FIG. 43. In a locked state, the tangs 232 of the retention cap 230 are positioned at least partially over the screw holes 214 of the lumbar plate as illustrated in FIG. 44.

After assembly of the lumbar plate system 200, the retention cap 230 may rotate (clock-wise or counterclock-wise) between the sets of the insertion-assembly slots 223, such as rotating every 45° between the relief detents 226 not circumferentially aligned with the insertion-assembly slots 223 and the relief detents 226 circumferentially aligned with the insertion-assembly slots 223. In the embodiment illustrated, in each of the unlocked and locked state of the lumbar plate system 200, the protrusions 237 are aligned with the relief detents 226 not circumferentially aligned with the insertion-assembly slots 223 and must rotate through the relief detents 226 circumferentially aligned with the insertion-assembly slots 223 to reach the other of the unlocked and locked state.

The retention cap 230 is prevented from rotating by the hard-mechanical stop of the inner diameter material of the hole circumferentially between the relief detents 226. The retention cap 230 cannot freely rotate without a driver instrument.

Disassembly is prevented by the clocked-position of the blind interference ribs 224 which capture the protrusions 237 during rotation of the retention cap 230.

From a lateral surgical approach, the surgeon will slide the lumbar plate system 200 down a central shaft instrument, or K-wire, that is inserted into the intervertebral space. The lumbar plate 210 is positioned relative to the vertebrae. The surgeon uses instrumentation to prepare the bone for bone screws 250. The surgeon drives the bone screws 250 through screw holes 214 of the lumbar plate 210 in an alternating 1-3-2-4 pattern. After all the bone screws 250 are seated within the screw holes 214, the surgeon will rotate the retention caps 230 to the desired position with the tangs 232 of the head 230 overlapping the heads of the bone screws 250. Each retention cap 230 will overhang the associated screw holes 214 to ensure the associated bone screws 250 cannot back-out.

During revision surgery, the retention cap 230 can be rotated either clockwise or counterclockwise until the tangs 232 of the head 230 do not overhang with the heads of the bone screws 250. Then the bone screws 250 can be removed, and finally the lumbar plate 210 is removed.

Figure 48:
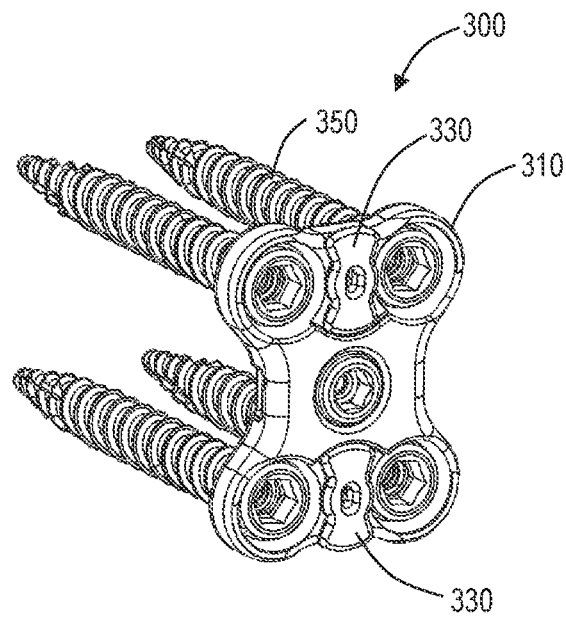
FIG. 48 is a perspective view of a further exemplary embodiment of the lumbar plate system of the present disclosure in an unlocked state.
Figure 49:
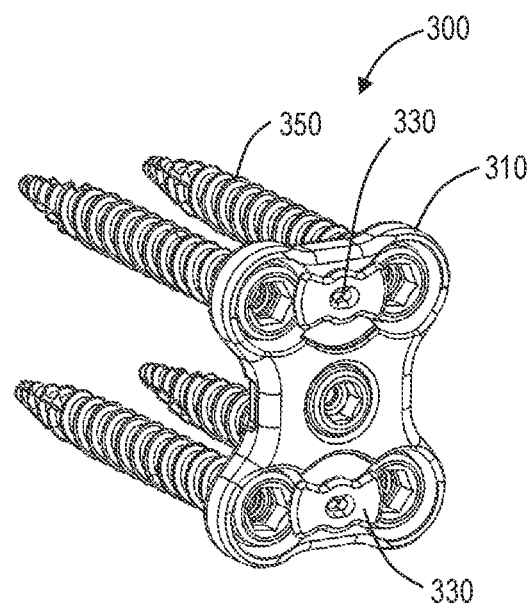
FIG. 49 is a perspective view of the lumbar plate system of FIG. 48 in a locked state.
Figure 50:
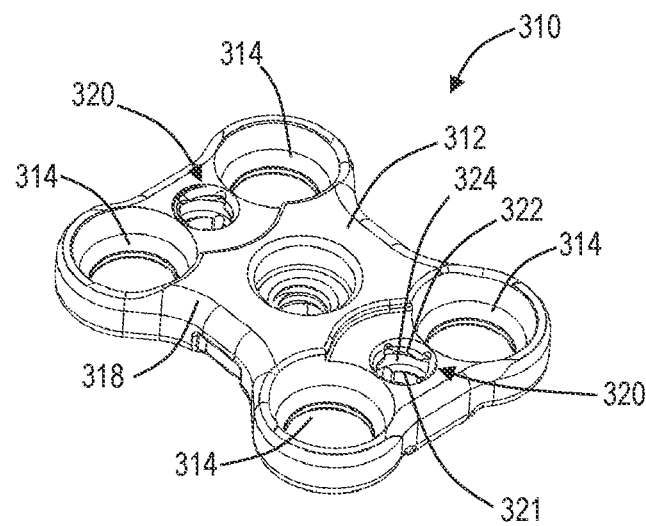
FIG. 50 is a perspective view of the lumbar plate of the lumbar plate system of FIGS. 48 and 49.
Figure 51:
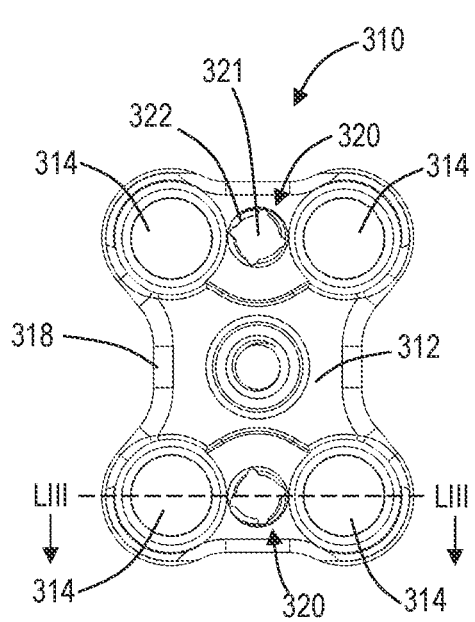
FIG. 51 is a top view of the lumbar plate of FIG. 49.
Figure 52:
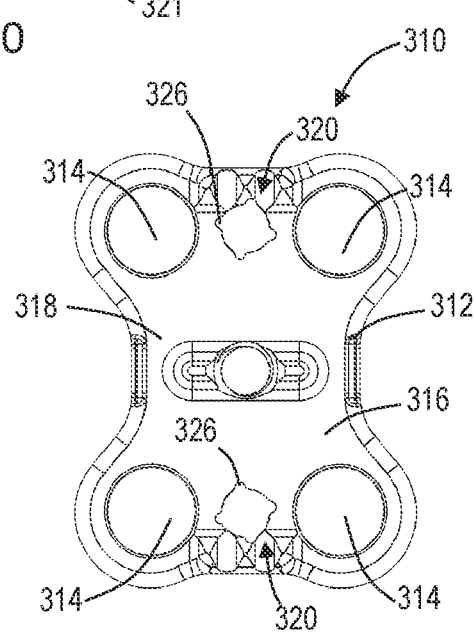
FIG. 52 is a bottom view of the lumbar plate of FIGS. 50-51.
Figure 53:
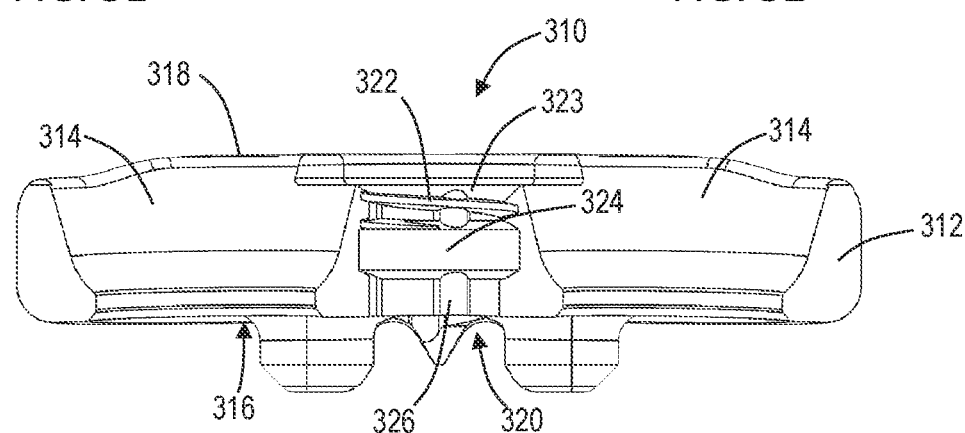
FIG. 53 is a cross-sectional view of the lumbar plate of FIGS. 50-52 taken along the line LIII-LIII in FIG. 51.
Figure 54:
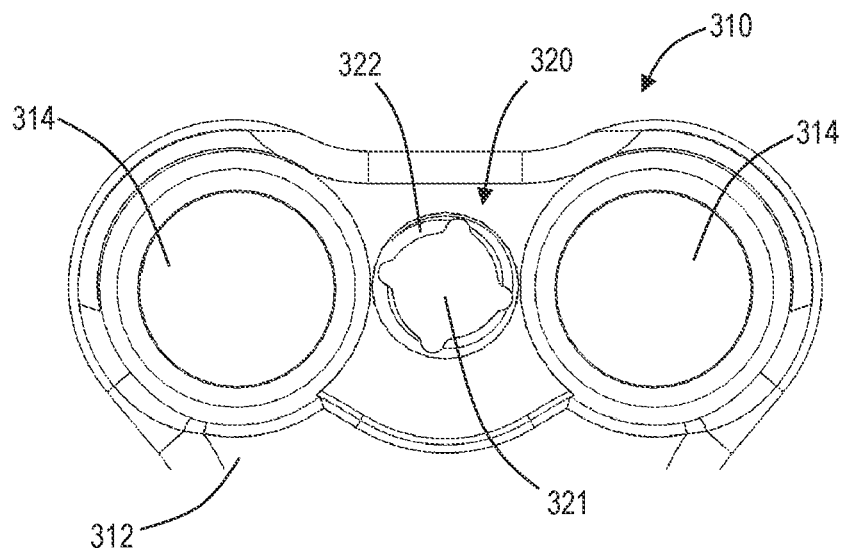
FIG. 54 is a detail top perspective of the lumbar plate of FIGS. 50-53.
Figure 55:
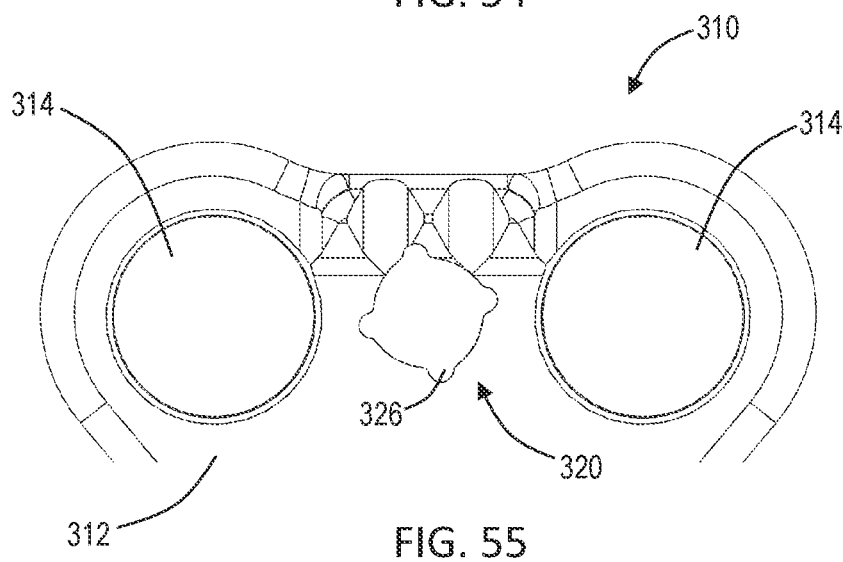
FIG. 55 is a detail bottom perspective of the lumbar plate of FIGS. 50-54.
Figure 56:
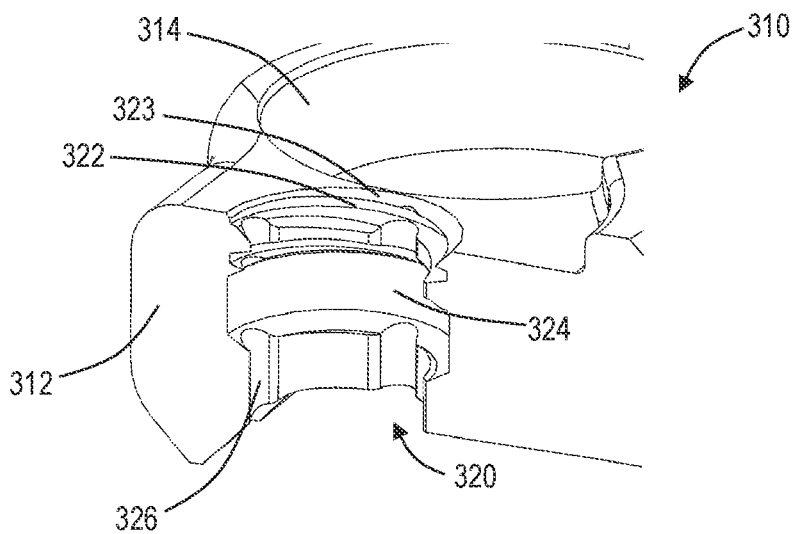
FIG. 56 is a cross-section of a perspective view of the lumbar plate of FIGS. 50-55.

FIGS. 48-68 illustrate a further exemplary embodiment of the lumbar plate system 300 of the present disclosure. Referring to FIGS. 48 and 49, the lumbar plate system 300 includes a lumbar plate 310, one or more retention caps 330, and bone screws 350. In the embodiment illustrated in FIGS. 48 and 49, the lumbar plate system 300 includes two retention caps 330 for securing the bone screws 350 in place relative to the lumbar plate 310.

FIGS. 50-56 illustrate the lumbar plate 310 of the lumbar plate system 300. Referring to FIGS. 50-56, in the embodiment illustrated, the lumbar plate 310 incudes a sagittal profile that is symmetric about the transverse and coronal planes. The lumbar plate 310 includes screw holes 314 formed in a body 312 thereof. In embodiments, the screw holes 314 consist of four poly-axial screw holes with a range of angulation optimized from screw fixation of the lateral lumbar. The screw holes 314 are positioned on an appropriately sized bolt-pattern relative to the central axis of the lumbar plate 310. In embodiments, the screw hole bolt pattern size is optimized to ensure integrity of the lumbar plate 310, enable surgical bone screw preparation, and reduce instances of screw contact interference between contiguous interbody levels with the same system. In embodiments, the lumbar plate 310 is a metallic plate formed of a biocompatible material.

Bone-interfacing surfaces 316 at a bottom of the lumbar plate 310 are concave and are adapted to conform to the typical anatomy of the lateral thoracolumbar vertebral bodies. Instrument-mating convex surfaces of the lumbar plate 310 are optimized for minimal plate thickness. Plate edges and transitions 318 are minimized to prevent soft-tissue irritation.

The lumbar plate 310 locking features 320 are holes 321 located in the coronal plane of the lumbar plate 310 and symmetric about the transverse plane. In the embodiment illustrated, the lumbar plate 310 includes two locking features 320. The locking features 320 are adapted to mate with a retention cap 330 and include a modified internal thread 322, a blind recess bore 324, and a clocking through star-pattern 326. The locking features 320 are intended to mate with one retention cap 330 each.

The internal thread 322 includes a lead-in surface 323 that is chamfered about a pre-drill hole to enable system assembly with the retention cap 330. The thread size of the internal thread 322 defines the size and shape of the blind recess bore 324 and clocking-star pattern 326. The thread major diameter and pitch diameter are traditional according to machinist guidelines. However, in embodiments, the minor diameter is increased to optimize the interface with the retention cap 330.

The blind recess bore 324 is below the internal thread lead-in surface 323 by a distance equal to at least one thread pitch. This distance ensures at least one thread within the central hole 321 of the lumbar plate 310 defined by the locking feature 320. The major diameter of the blind recess bore 324 is equal to, or greater than the major diameter of the internal thread 322 but the difference is minimized. The top and bottom vertices of the blind recess bore 324 are chamfered equivalent to the thread-form angle (i.e., typically) 60°.

The clocking star-pattern 326 is below the blind recess bore 324. The height of the clocking-star pattern 326 is optimized and adapted for mechanism functional integrity. The clocking star-pattern 326 is defined by axially symmetric cut-outs 327 spaced evenly about an axis 360-degree of rotation of the central hole 321. The position of the cut-outs 327 can be optimized for preferred rotational control at defined angular intervals (i.e., factors of 360). The extent of the cut-outs 327 major diameter is optimized relative to the minor diameter of the central hole 321, the central hole 321 being a through hole. However, the major diameter of the cut-outs 327 is coincident with the major diameter of the blind recess bore 324. The cut-out geometry transitions from the major diameter thereof to the minor diameter of the central hole 321, which is equivalent to the modified minor diameter of the internal thread 322.

FIGS. 57-60 illustrate the retention cap 330 of the lumbar plate system 300. Referring to FIGS. 57-60, the retention cap 330 includes a head 331 and a shank 335. In embodiments, the retention cap 330 is formed of metal. In embodiments, the head 331 includes a bilateral profile to maximize or minimize exposure based on the functional rotational alignment of the retention cap 330. A thickness of the head 331 is adapted to prevent deflection thereof to prevent screw back-out when the lumbar plate system 300 is in a locked state. In the embodiment illustrated, the head 331 does not extend beyond the overall thickness of the lumbar plate 310 when assembled thereto.

The head 331 includes tangs 332 or tabs (one for each screw hole 314 of the lumbar plate 310 that will be at least partially covered by the retention cap 330). In the embodiment illustrated, the head 331 includes two tangs and includes a bowtie like shape. In embodiments, the profile shape of the tangs 332 is optimized for maximum screw 350 head coverage when the lumbar plate 300 is in a locked state.

The shank 335 includes an external thread 336, two or more protrusions 337, and relief cut-outs 338. The external thread 336 is adapted to mate with the internal thread 322 of the lumbar plate 310. The external thread 336 is of minimal height (i.e., turns) and modified major outer diameter. The major diameter of the external thread 336 may be increased or decreased depending on the system manufacturing assembly method. However, the external thread 336 major diameter is maximized for optimum material interference with the plate internal thread 322 for disassembly prevention. In embodiments, the two or more protrusions are teeth, symmetric, and evenly spaced about the central axis 360-degree of rotation (i.e., factors of 360) of the shank 335.

The relief cut-outs 338 are orthogonal to the central axis of the shank 335, extending from an end of the shank 335 towards the head 332. The size and height of the relief cut-outs 338 is such to allow the shank 335 to deflect inward when compressing the two or more protrusions 337. The relief cut-outs 338 are clocked relative to the two or more protrusions, such as at 90° or half the angular distance between the protrusions.

The retention cap 330 includes a screw drive 333 formed therein. In embodiments, the screw drive 333 is one of a slotted drive, a cruciform drive, a square drive, an internal hex drive, and the like. The screw drive 333 can be formed in the head 331, the shank 335, or a combination thereof. In the embodiment illustrated, the screw drive 333 includes a female cut-out that interfaces with a driver instrument and is recessed in a counter-bore hole 334 formed in head 331. The counter-bore hole 334 creates a shoulder about the screw drive 333 and acts as a mechanical stop for which surgical instrumentation (i.e., hex driver, screwdriver, and the like) can interface. In embodiments, the female cut-out of the screw drive 333 extends at least partially through the long axis of the shank 335.

Figure 61:
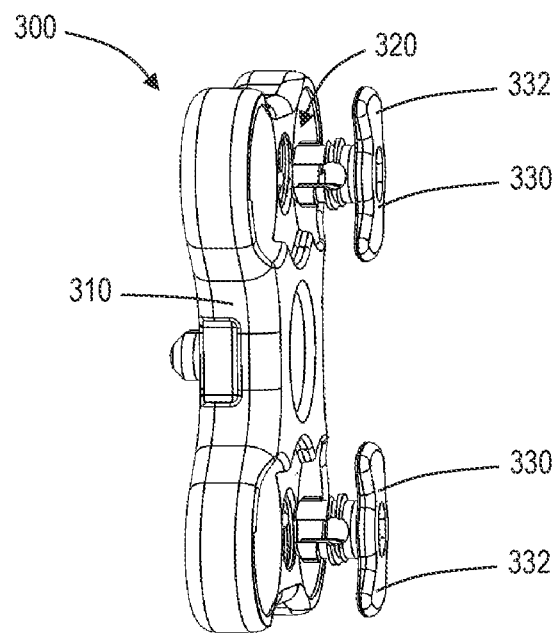
FIG. 61 is a perspective view of the lumbar plate system of FIGS. 48 and 49 illustrating an initial insertion of the retention caps into the lumbar plate.
Figure 62:
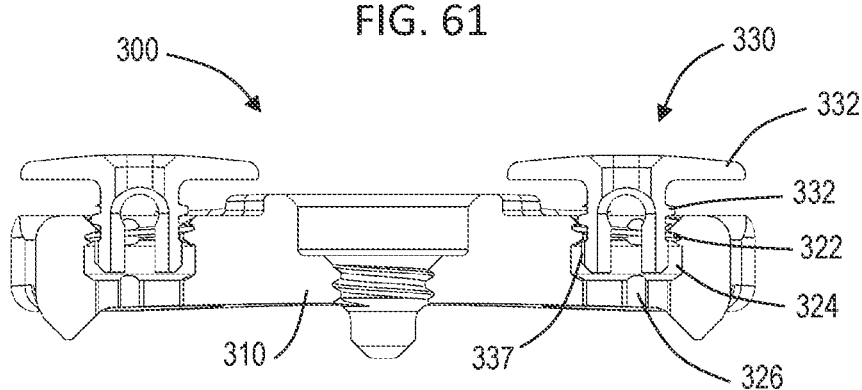
FIG. 62 is a cross-sectional view of a portion the lumbar plate system of FIG. 61 illustrating the initial insertion of a retention cap into the lumbar plate.
Figure 63:
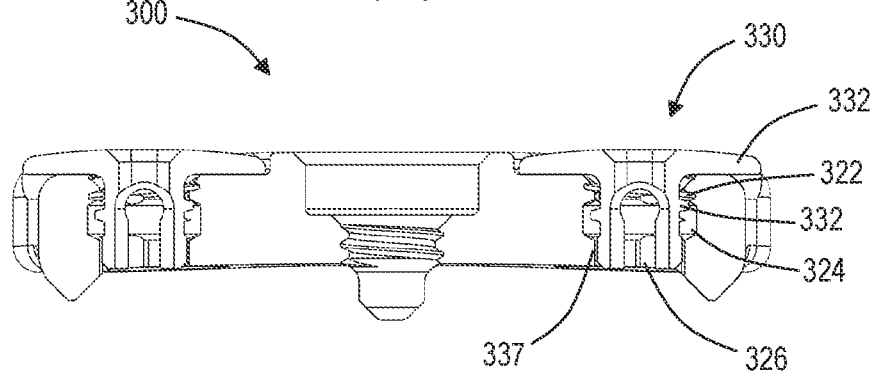
FIG. 63 is a cross-sectional view of the lumbar plate system of FIGS. 48 and 49 illustrating the completed insertion of a retention cap into the lumbar plate.

FIGS. 61-63 illustrate assembly of the lumbar plate system 300. In embodiments, each retention cap 330 assembles to the lumbar plate 310 during manufacturing and prior to surgical usage. Referring to FIGS. 61-63, first, the protrusions 337 of the retention cap 330 are inserted into the matching clocking star-pattern 326 of the lumbar plate 310 until the external thread 336 of the retention cap 330 dead-stops against the internal thread 322 of the lumbar plate 310. The protrusions 337 have an external minor diameter slightly greater (i.e., slip-fit interference) than an internal minor diameter of the clocking star-pattern 326. The external minor diameter of the protrusions 337 will interfere with the internal minor diameter of the clocking star-pattern 326 prior to the dead-stopping of the external thread 336 of the retention cap 330.

Next, the retention cap 330 is rotated in a threading direction to engage with the central hole 321. During rotation, and as the shank 335 of the retention cap 330 travels axially into the central hole 321 of the lumbar plate 310, the protrusions 337 will deflect inward and release with the cut-outs 326 of the clocking star-pattern 326. After successful thread-rotation, the thread engagement is relieved when the external thread 336 of the retention cap 330 recedes into the blind recess bore 324 of the lumbar plate 310, which is below the internal thread 322 of the lumbar plate 310. There is minimal clearance between the major diameter of the external thread 336 and the internal major diameter of the blind recess bore 324. In embodiments, line-to-line contact is acceptable.

In embodiments, the blind recess bore 324, and in combination with the dimensions of the position of the external thread 336 of the retention cap along the shank 335 of the retention cap 330 relative the thread depth of the internal thread 322 of the lumbar plate 310, is adapted to enable application of axial compression to the retention cap 330 with the lumbar plate 310. This is due to the external thread 336 interfacing with the blind recess bore 324, and in particular, a proximal chamfer surface of the blind recess bore 324 opposing the external thread 336. In embodiments, this interference relationship prevents the retention cap 330 from axial travel, or displacement, during clockwise rotation thereof.

Figure 64:
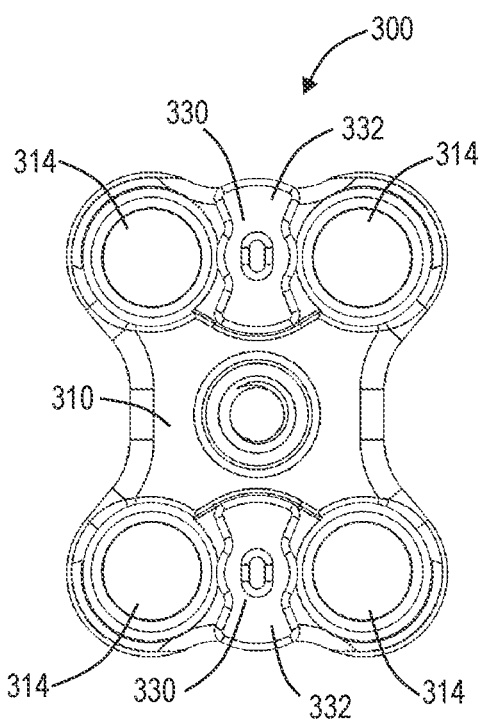
FIG. 64 is a top view of the lumbar plate system of FIGS. 48 and 49 illustrating the retention caps in an unlocked position in the lumbar plate.
Figure 65:
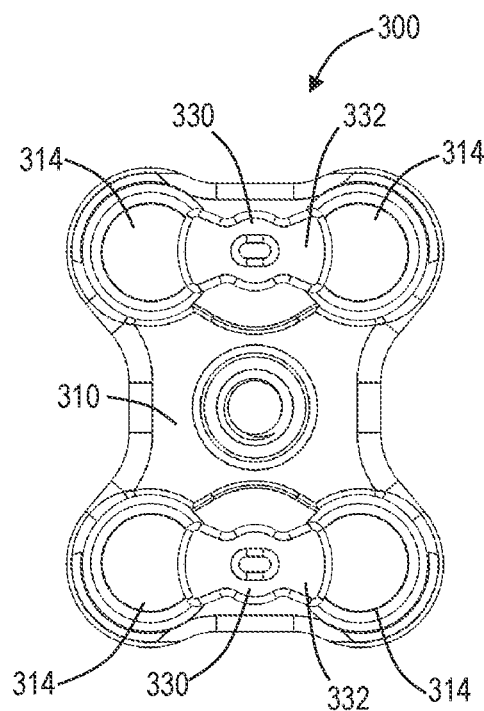
FIG. 65 is a top view of the lumbar plate system of FIGS. 48 and 49 illustrating the retention caps in a locked position in the lumbar plate.

FIGS. 64-68 illustrate the usage and function of the lumbar plate system 300. Referring to FIGS. 64 and 65, in an assembled and unlocked state, the tangs 332 of the retention cap 330 are positioned between the screw holes 314 of the lumbar plate 310. In a locked state, the tangs 332 of the retention cap 330 are positioned at least partially over the screw holes 314 of the lumbar plate 310.

Figure 66:
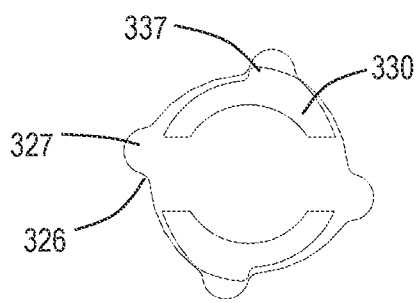
FIG. 66 illustrates a radial interference between a shank of the retention caps and a cut-out of the lumbar plate while a retention cap is in the unlocked state.
Figure 67:
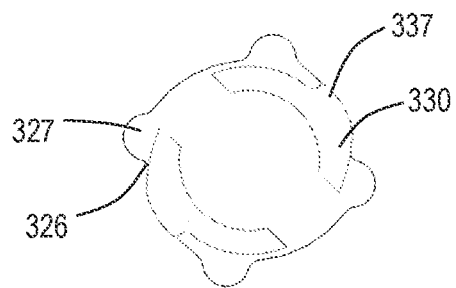
FIG. 67 illustrates a radial interference between a shank of the retention cap and a cut-out of the lumbar plate while a retention cap is in an intermediate state.
Figure 68:
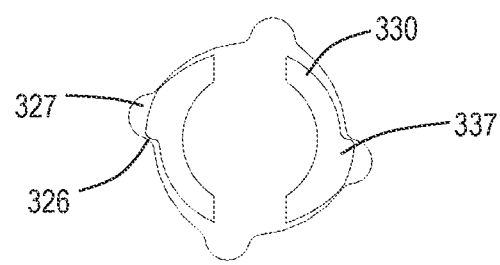
FIG. 68 illustrates a radial interference between a shank of the retention cap and a cut-out of the lumbar plate while a retention cap is in the locked state.

Referring to FIGS. 66-68, the configuration of the clocking star-pattern 326 and the protrusions 337 is adapted to control axial rotation of the retention cap 330 relative to the lumbar plate 310, and in particular about a central axis of the central hole 321. During rotation, the protrusions 337 deflect the shank 335 of the retention cap 330 due to increasing rotational interference between the cut-outs 327 of the clocking star-pattern 326.

In the embodiment illustrated, the retention cap 330 rotates only in one direction after assembly of the retention cap 330 to the lumbar plate 310. In particular, the protrusions 337 interface with the cut-outs 327 of the clocking star-pattern 326 to prevent rotation in an opposing direction by a hard-mechanical stop defined by the cut-outs 327 and the protrusions 337. This configuration is adapted to permit rotation of the retention cap 330 in the threading direction and to oppose rotation in the opposing direction (the unthreading direction). Thus, the protrusions 337 and the clocking star-pattern 326 are adapted such that the functional rotation for rotating the retention cap 330 between the unlocked and lock states is in the rotational direction that matches the thread rotation used for assembling the retention cap 330 to the lumbar plate 310. Because the retention cap 330 cannot rotate in the opposing direction, the retention cap 330 cannot disassemble by means of the previously aforementioned thread-engagement.

In embodiments, the threading direction is right-handed (clockwise) and the protrusions 337 and the clocking star-pattern 326 are adapted to permit rotation in the right-handed direction and to oppose rotation in the left-handed (counterclockwise) direction. However, in other embodiments, the lumbar plate system 300 is in a left-handed configuration for the threading and functional rotation of the retention cap 330 and the right-handed rotation thereof is opposed by the configuration of the protrusions 337 and the clocking star-pattern 326.

The retention cap 330 does not freely rotate in the one direction (the threading direction) when assembled with the lumbar plate 310. The two or more protrusions 337 have external minor diameter slightly greater than (i.e., slip-fit interference) the internal minor diameter of the clocking star-pattern 326. Surface interference between the components provides resistance to rotation of the cap in the one direction.

The major diameter of the two or more protrusions 337 is less than the major internal diameter of the cut-outs 327 of the clocking star-pattern 326. This ensures the shank 332 of the retention cap 330 can release when the position of the protrusions 337 aligns with the cut-outs 327 of the clocking star-pattern 326.

From a lateral surgical approach, the surgeon will slide the lumbar plate system 100 down a central shaft instrument, or K-wire, that is inserted into the intervertebral space. The lumbar plate 310 is positioned relative to the vertebrae. The surgeon uses instrumentation to prepare the bone for the bone screws 350. The surgeon drives the bone screws 350 through the screw holes 314 of the lumbar plate 310 in an alternating 1-3-2-4 pattern. After all bone screws 350 are seated within the screw holes 314, the surgeon will rotate the retention cap 330 to the desired position with the tangs 332 overlapping the head of each of the bone screws 350. The retention cap 330 will overhang the screw holes 314 to ensure the bone screws 350 cannot back-out.

During revision surgery, the retention cap 330 can be rotated until the tangs 132 do not obstruct the screw holes 314. Then the bone screws 350 can be removed, and finally the lumbar plate system 300 is removed.

While the embodiments disclosed herein only show lumbar plate systems with one or two retention caps, other embodiments are also contemplated, including embodiments with three or more retention caps, such as an embodiment with the centrally located retention cap (FIGS. 1-23) and with the symmetrically positioned retention caps (FIGS. 24-68) that function to simultaneously secure the bone screws in their seated positions.

Although the present disclosure has been illustrated and described herein with reference to preferred embodiments and specific examples thereof, it will be readily apparent to those of ordinary skill in the art that other embodiments and examples may perform similar functions and/or achieve like results. All such equivalent embodiments and examples are within the spirit and scope of the present disclosure, are contemplated thereby, and are intended to be covered by the following claims.

What is claimed is:

1. A plate system for securing to a vertebrae or other osseous material, the plate system comprising:
    a plate comprising:
        screw holes formed therein adapted to receive bone screws, and
        a locking feature including:
            a plurality of axially extending insertion-assembly slots proximal a top surface of the plate and adapted to guide protrusions of an associated retention cap into the locking feature,
            a plurality of relief detents defined in the plate and positioned distal to the top surface of the plate and adapted to receive the protrusions of the associated retention cap and interfere with rotational movement of the associated retention cap, and
            a plurality of blind interference ribs positioned adjacent to the plurality of relief detents closer to the top surface of the plate than the plurality of relief detents, the plurality of blind interference ribs adapted to prevent axial movement of the associated retention cap.

2. The plate system of claim 1, wherein each blind interference rib of the plurality of blind interference ribs circumferentially spans between two axially extending insertion-assembly slots of the plurality of axially extending insertion-assembly slots.

3. The plate system of claim 1, further comprising:
    a retention cap associated with the locking feature, the retention cap comprising:
        a head including tangs, and
        a shank extending from the head, the shank including protrusions distal to the head and relief cut-outs extending towards the head from an end of the shank distal to the head, the relief cut-outs being clocked relative to the protrusions,
    wherein, in a first rotational alignment of the retention cap relative to the plate, the tangs are positioned between screw holes so as to not axially overlap with the screw holes, and, in a second rotational alignment of the retention cap relative to the plate, the tangs are positioned at least partially over the screw holes.

4. The plate system of claim 3, wherein retention cap is configured to rotate both clockwise and counterclockwise between the first rotational alignment and the second rotational alignment.

5. The plate system of claim 3, wherein the protrusions of the shank include a plurality of male detents.

6. The plate system of claim 3, wherein the plurality of axially extending insertion-assembly slots circumferentially align with a set of female detents of the plurality of relief detents, the axially extending insertion-assembly slots being adapted to guide the protrusions of the retention cap through the locking feature to the set of female detents.

7. The plate system of claim 6, wherein the plurality of relief detents includes a second set of female detents clocked from the first set of female detents and the insertion-assembly slots, wherein each female detent of the second set of female detents is positioned under a blind interference rib of the plurality of blind interference ribs and is adapted to receive a protrusion of the protrusions while the retention cap is in the second rotational alignment.

8. The plate system of claim 7, wherein material of the plate positioned between the plurality of relief detents is configured to prevent unintentional rotation of the retention cap between the first rotational alignment and the second rotational alignment, and wherein the material of the plate positioned between the plurality of relief detents is configured to allow rotation of the retention cap between the first rotational alignment and the second rotational alignment with the use of a driver instrument.

9. The plate system of claim 3, wherein the shank of the retention cap further comprises a shoulder proximal the head of the retention cap, wherein the plate further comprises a diametric shoulder proximal to the top surface of the plate, and
    wherein the shoulder of the retention cap and the diametric shoulder of the plate are configured to form a slip-fit condition such that the retention cap self-centers relative to the plate during assembly.

10. The plate system of claim 3, wherein the plate further comprises:
    a lead-in chamfer defined in the top surface of the plate and configured to guide the shank of the retention cap into the locking feature.

11. A plate system for securing to a vertebrae or other osseous material, the plate system comprising:
a plurality of retention caps, each retention cap comprising:
a head including tangs, and
a shank extending from the head, the shank including protrusions distal to the head and relief cut-outs extending towards the head from an end of the shank distal to the head, the relief cut-outs being clocked relative to the protrusions; and
a plate comprising:
screw holes formed therein adapted to receive bone screws, and
a plurality of locking features, each locking feature associated with one retention cap of the plurality of retention caps and including:
a plurality of axially extending insertion-assembly slots proximal a top surface of the plate and adapted to guide protrusions of the associated retention cap into the locking feature,
a plurality of relief detents defined in the plate and positioned distal to the top surface of the plate and adapted to receive the protrusions of the associated retention cap and interfere with rotational movement of the associated retention cap, and
a plurality of blind interference ribs positioned adjacent to the plurality of relief detents closer to the top surface of the plate than the plurality of relief detents, the plurality of blind interference ribs adapted to prevent axial movement of the associated retention cap,
wherein, in a first rotational alignment of each retention cap relative to the plate, the tangs are positioned between screw holes so as to not axially overlap with the screw holes, and in a second rotational alignment of each retention cap relative to the plate, the tangs are positioned at least partially over the screw holes.

12. The plate system of claim 11, wherein each blind interference rib of the plurality of blind interference ribs circumferentially spans between two axially extending insertion-assembly slots of the plurality of axially extending insertion-assembly slots.

13. The plate system of claim 11, wherein each retention cap of the plurality of retention caps is configured to rotate both clockwise and counterclockwise between the first rotational alignment and the second rotational alignment.

14. The plate system of claim 11, wherein the plurality of locking features includes a first locking feature and a second locking feature that are symmetric about a transverse plane of the plate.

15. The plate system of claim 11, wherein the tangs of the head of each retention cap of the plurality of retention caps define a bowtie shape.

* * * * *